(12) United States Patent
Hershline

(10) Patent No.: US 7,902,174 B2
(45) Date of Patent: Mar. 8, 2011

(54) ANTIVIRAL COMPOSITION

(76) Inventor: Roger Hershline, Charlotte, NC (US)

( * ) Notice: Subject to any disclaimer, the term of this patent is extended or adjusted under 35 U.S.C. 154(b) by 0 days.

(21) Appl. No.: 12/322,852

(22) Filed: Feb. 6, 2009

(65) Prior Publication Data
US 2009/0286757 A1    Nov. 19, 2009

(51) Int. Cl.
*A61K 31/715* (2006.01)
*A61K 31/721* (2006.01)
*C08B 37/02* (2006.01)

(52) U.S. Cl. ............. 514/58; 514/59; 536/103; 536/112

(58) Field of Classification Search ............... 514/58, 514/59; 536/103, 112
See application file for complete search history.

(56) References Cited

U.S. PATENT DOCUMENTS

| | | | |
|---|---|---|---|
| 5,250,520 A * | 10/1993 | Kurita et al. | 514/58 |
| 5,439,892 A * | 8/1995 | Davies | 514/58 |
| 6,821,958 B1 * | 11/2004 | Hershline | 514/58 |

OTHER PUBLICATIONS

TheMerck Manual, 16th Edn., 1999, pp. 52-55 and 85-86.*
Goodman and Gilman's "The Pharmacological Basis of Therapeutics", 10th Edn., 1996, pp. 54-57.*
Murakami et al, Sen'i Gakkaishi, 1995, 51 (12), 571-579.*

* cited by examiner

*Primary Examiner* — Shaojia Anna Jiang
*Assistant Examiner* — Ganapathy Krishnan
(74) *Attorney, Agent, or Firm* — Barbara E. Johnson, Esq.

(57) ABSTRACT

Chemical compounds, being the alkyl sulfate of sulfated saccharides, particularly, dextrin, dextran, and cyclodextrin, and pharmaceutical compositions containing these compounds. The compounds of the invention provide antiviral activity, particularly in the treatment and prevention of sexually-transmitted diseases. Methods of treating viral infection and preventing viral transmission include administration include administration of the compounds of the invention orally, topically, subcutaneously, by muscular injection, by intraperitoneal injection and by intravenous injection.

12 Claims, 7 Drawing Sheets

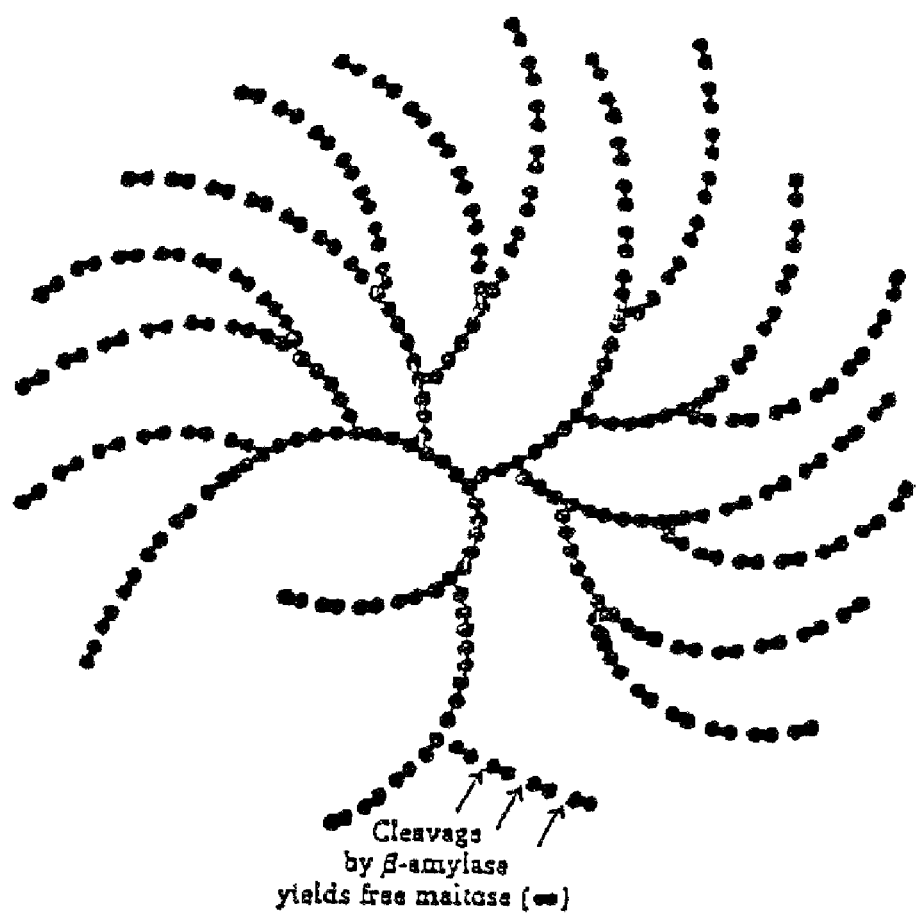
Fig. 1. Pictorial illustration of dextrin.

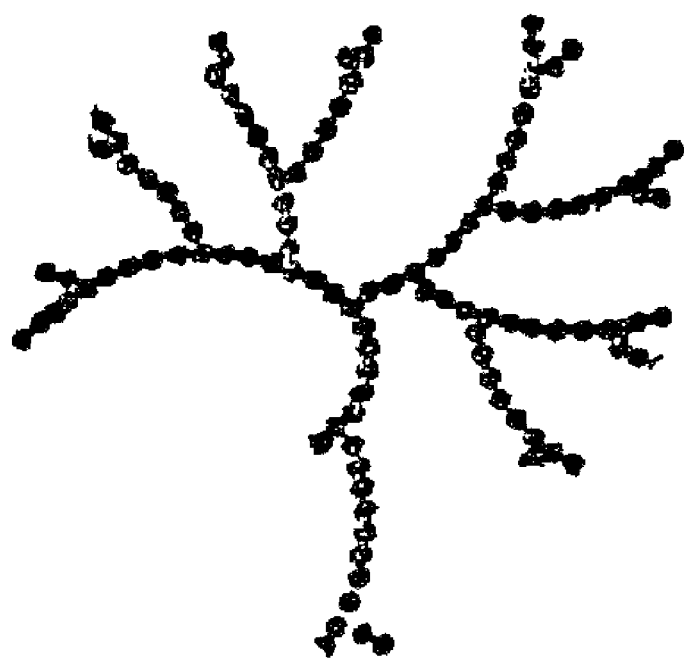
● = glucose
●● = maltose
Fig. 2. Pictorial illustration of a limit dextran.

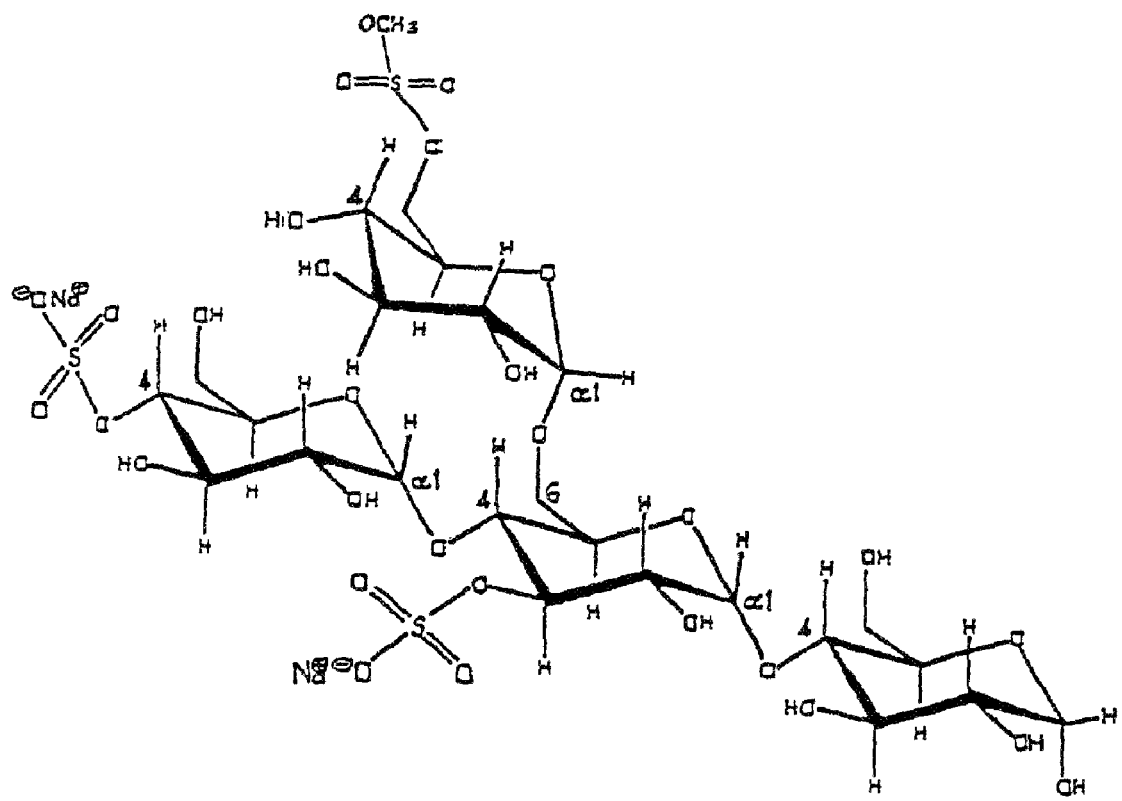
Fig. 3. Chemical structure for polysulfated polymethylsulfated dextrin.

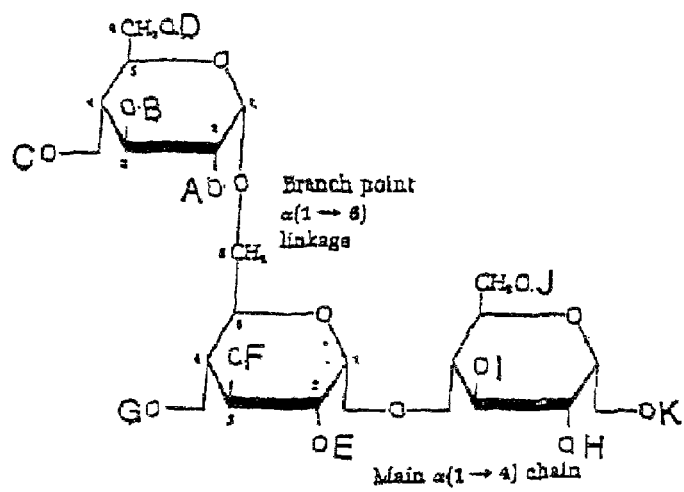
STRUCTURE 1
Fig. 4. A polysulfated polymethylsulfated dextrin compound (Structure 1) linked to a branch point glucose molecule with an α 1 → 6 linkage.

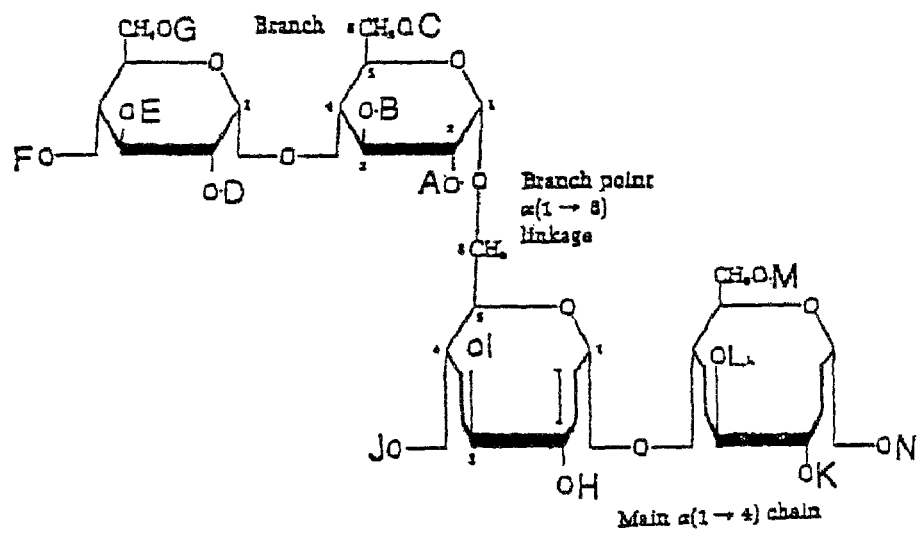
STRUCTURE 2
Fig. 5, A polysulfated polymethylsulfated dextrin compound (Structure 2) linked to a branch point maltose molecule with an α 1 → 6 linkage.

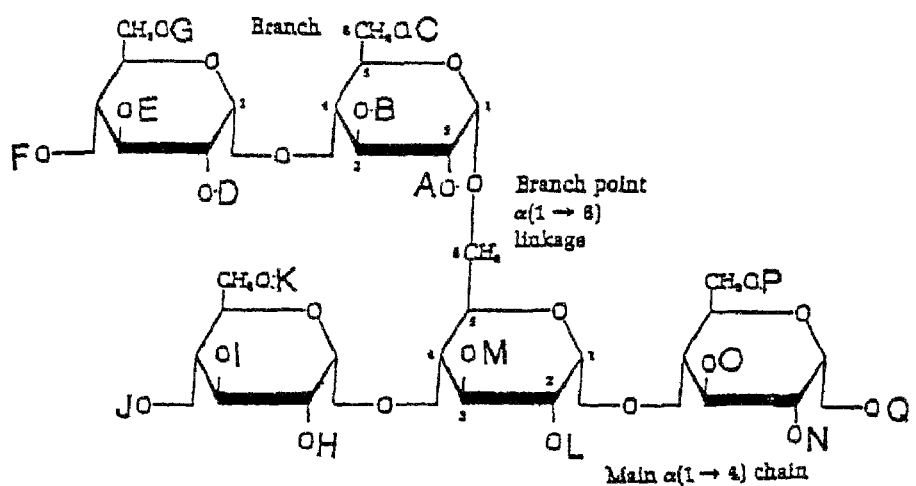
STRUCTURE 3
Fig. 6. A polysulfated polymethylsulfated dextrin compound (Structure 3) linked to a branch point maltose molecule with an α 1 → 6 linkage and linked to a branch point glucose molecule with an α 1 → 4 linkage.

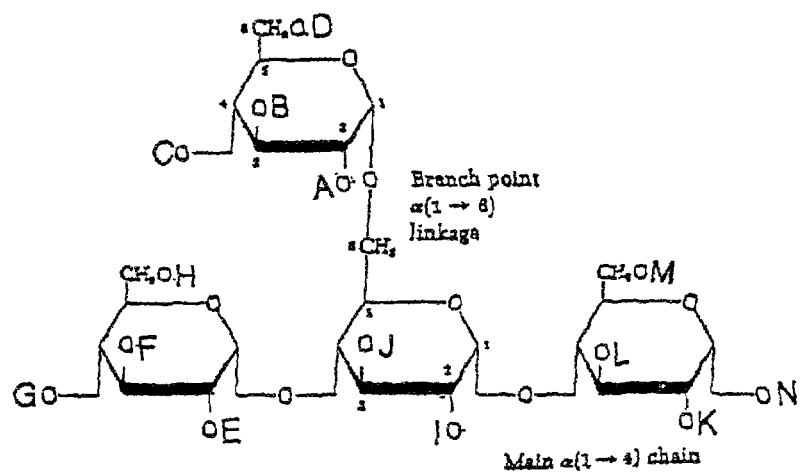
STRUCTURE 4
Fig. 7. A polysulfated polymethylsulfated dextrin compound (Structure 4) linked to a branch point glucose molecule with an α 1 → 6 linkage and linked to a branch point glucose molecule with an α 1 → 4 linkage.

ANTIVIRAL COMPOSITION

CROSS REFERENCE TO RELATED APPLICATIONS

This application claims the benefit of U.S. patent application Ser. No. 10/157,787, filed May 29, 2002, which claims priority to U.S. patent application Ser. No. 10/092,021, filed Mar. 6, 2002, which claims priority to U.S. Provisional Patent Application Nos. 60/288,032, filed May 2, 2001; and 60/273,724, filed Mar. 6, 2001, all of which are incorporated herein by reference.

BACKGROUND OF THE INVENTION

1. Field of the Invention

The present invention relates to the production of the alkyl sulfate of sulfated dextrin, the production of the alkyl sulfate of sulfated dextran, and to the use of these compounds to provide antiviral activity, particularly in the treatment and prevention of sexually-transmitted diseases.

2. Description of Related Art

Compounds exhibiting activity against viruses may function by a number of mechanisms: they may kill or disable the disease pathogens, they may inhibit the entry of the pathogen into cells, or they may prevent replication of the pathogen once it has entered a cell. All of these mechanisms are being studied to prevent and treat viral infection, including those resulting in diseases that can be sexually transmitted, such as Acquired Immunodeficiency Disease Syndrome (AIDS).

The generally accepted theory is that AIDS is caused by the Human Immunodeficiency Virus (HIV). There are two different versions of HIV: HIV-1 and HIV-2. These viruses are believed, on the basis of their genetic sequences, to have evolved from the Simian Immunodeficiency Virus (SIV), with HIV-2 being much more similar to SIV. Several years after the initial HIV infection, the immune system is weakened to the point where opportunistic infections occur, resulting in the syndrome of AIDS.

Research has revealed a great deal of valuable medical, scientific, and public health information about HIV and AIDS. HIV molecules whose structures are known include reverse transcriptase (RT), proteases of HIV-1 and HIV-2, the catalytic domain of HIV integrase (INT), the HIV matrix protein, the HIV capsid protein and several fragments of CD4. HIV macromolecules whose structures are being investigated include the surface glycoproteins (gp160, gp120, gp41), and the regulatory proteins (tat, rev, vpr, tar).

The ways in which HIV can be transmitted have been clearly identified. HIV is spread by sexual contact with an infected person, by sharing needles and/or syringes (primarily for drug injection) with someone who is infected, or through transfusions of infected blood or blood clotting factors. Babies born to HIV-infected women may become infected before or during birth or through breast-feeding after birth. In the health care setting, workers have been infected with HIV after being stuck with needles containing HIV-infected blood or, less frequently, after infected blood gets into a worker's open cut or a mucous membrane (for example, the eyes or inside of the nose). HIV is found in varying concentrations or amounts in blood, semen, vaginal fluid, breast milk, saliva, and tears.

In recent years, medical science has made great progress in the ability to successfully treat the opportunistic infections associated with HIV infection. Wider use of medications for preventing tuberculosis, *Pneumocystis carinii* pneumonia (PCP), toxoplasmosis, and *Mycobacterium avium* complex (MAC), for example, has helped reduce the number of people with HIV who develop serious illness and die from AIDS.

Also, several classes of compounds have been federally approved to treat HIV infection. These include nucleoside RT inhibitors (AZT, ddI, ddC, d4T and 3TC), non-nucleoside RT inhibitors (alpha-APA, TSAO, costatolide, TIBO, UC10), protease inhibitors (indinavir, saquinavir, KNI 272), attachment inhibitors (sulfate polysaccharides, sulfonated dyes) and neutralizing antibodies. Combinational therapy with these drugs seems to produce the best results, reducing the level of HIV particles circulating in the blood (viral load) to very low levels in many individuals.

Though treatment results using these drugs have been encouraging, the virus is not eliminated, these drugs do not work for all people, there are adverse interactions with other medications, toxicity to the drugs is problematic, dosing protocols are complex, resistance to treatment develops, and expense is extremely high. Furthermore, long-term effectiveness and safety are completely unknown. Clearly, there remains a need for new therapies.

Attempts to develop a vaccine have not been successful to this point.

Testing facilities perform in vitro analyses to identify compounds with antiviral activity. Therapeutic indices of active compounds are evaluated using several viral strains. Many viruses are routinely available for the testing of compounds for antiviral activity in viruses other than HIV, including the herpesviruses HSV-1, HSV-2, HCMV, VZV and EBV; the respiratory viruses Flu A, Flu B, RSV, Paraflu 3 and Ad5; measles and hepatitis B virus. Anti-HIV assays are routinely performed in established cell culture lines. Recently fresh human peripheral blood lymphocytes (PBMCs) have been introduced as test media.

Assays measure the ability of compounds to directly inactivate the HIV virus and inhibit HIV-induced cell killing through numerous enzyme-inhibiting mechanisms (Reverse Transcriptase, RNaseH, Integrase, Protease, Tat, Rev and Nef), by preventing attachment and internalization (inhibit gp120-CD4 interaction) or by inhibiting regulatory protein expression, or by inhibiting maturation and budding, or by preventing Syncytical formation. Toxicity of the test compounds to host cells is also measured. It is generally accepted that if the test compound is highly toxic to cells, then it will have little value despite anti-HIV activity.

Infectious virus levels are measured by viral titers, quantitation of p24 (a viral protein found to be proportional to viral concentration) or measurement of the activity of the viral enzymes.

Several parameters are routinely varied to more completely understand the potential of a particular drug. The concentration of a drug is varied to calculate the ED50 (Effective Dose at 50% inhibition), LD50 (Lethal Dose at 50% cell death), and TI50 (Therapeutic Index, which is the Effective Dose divided by the Lethal Dose).

The concentration of the initial viral load is varied in the cell system used for testing to help determine drug potency. The time of drug addition to the cell system, either pre- or post-infection, is varied to identify strengths and weaknesses in the drug mechanism of action. Another test is to add the drug to the cell system and then wash it away before infection. This gives insight into cell-drug mechanisms of action. Topical assays test drugs which may be of use as preventive barriers. Both viral killing and cellular toxicity are measured in these assays.

Active anti-HIV compounds will likely be used in combination with other anti-HIV agents, with agents that inhibit opportunistic agents, or with other therapies. Therefore, the compounds are tested with all known useful drugs to determine beneficial synergistic effects or possible harmful combinatorial toxicity.

Drugs that prove to be successful in in vitro testing are selected for animal testing. Several animal models have proven to be helpful including systems using the mouse, cat, and rhesus macaque. The test compound and virus can be administered by a variety of methods and routes in addition to the variables discussed above. Animal mucosal models of HIV transmission may be useful for the evaluation of possible therapeutic agents. Test compounds that may have limited effectiveness in fully developed HIV may be effective at the time of initial infection. Models are useful in exploring this possibility. Animal models traditionally have been used for the pre-clinical evaluation of lead compounds to determine mechanism of action, distribution, toxicity, and efficacy.

Antiviral compounds are also being investigated for use as microbicides. A "microbicide" is any substance that can substantially reduce transmission of sexually transmitted infections (STIs) when applied either in the vagina or rectum. Target viruses include herpes viruses such as cytomegalovirus and herpes simplex, hepatitis agents, and the papilloma virus. Proposed forms for microbicides include gels, creams, suppositories, films, and sponges or vaginal rings that slowly releases the active ingredient over time. Microbicides are not currently available commercially, but a number of compounds, including nonoxynol-9, cellulose sulfate, carrageenan, cyanovirin, the sulfated polysaccharide PRO2000 and dextrin sulfate, are currently being evaluated. Dextrin sulfate has been found to have a high level of toxicity. Nonoxynol-9 has been found to cause inflammation of mucosa that may actually enhance the chance of infection. There remains a need for a proven effective nonirritant antiviral compound of low toxicity for use as a microbicide.

Polysulfonated polysaccharides (PSP) have been previously proposed to be used to treat HIV infection. The most studied include curdlan sulfate (CDS), dextrin sulfate, dextran sulfate (DS), and heparin sulfate. Many of these, including dextran sulfate, curdlan sulfate and dextrin 2-sulfate, have been studied in human trials. Many other naturally occurring isolated sulfates have been shown to inhibit the AIDS virus. Smaller non-polymeric sulfated sugar based compounds included pentosan sulfate and glucosamine sulfate.

Though the results indicate that sulfates are a viable lead for the development of an anti-HIV drug, several problems remain. Firstly, the large anionic structures of the PSPs show very poor absorption or no absorption from oral administration. Secondly, when PSP's are given intravenously the toxic effects of seriously decreasing the amount of platelets and decreasing the ability of blood to clot become limiting factors. Oral administration is also related to serious gastrointestinal toxic effects including the possible development of cancers demonstrated in rodents. Furthermore, there is no protection of the compounds from sulfatase enzymes which rapidly degrade these compounds and shorten the half-life.

The use of dextrin-2 sulfate as an anti-HIV compound versus generically sulfated dextrin (that is sulfates at any or all of the 2, 3 or 6 positions of the glucose units) has also been proposed. The use of dextrin-2 sulfate is an attempt to decrease toxicity while maintaining anti-HIV activity. Recent attempts to administer dextrin-2 sulfate by intra-peritoneal administration (that is, infusion into the body cavity by a catheter passing through the abdominal wall as done in peritoneal dialysis) shows some promise in decreasing HIV infection while decreasing intravenous-type side effects. However, the intra-peritoneal method introduces extremely little if any drug to the systemic circulation and relies upon the lymphatic circulation to expose circulating HIV infected white blood cells to the drug as they pass through the peritoneal cavity. Evaluation of dextrin 2-sulfate shows that the anti-platelet effect and anti-coagulant effect persists and there is no attempt at chemical inhibition of the hydrolysis of the drug by hydrolyzing enzymes. Consequently, dextrin 2-sulfate has not been shown to provide significant advantages over dextrin sulfate.

Accordingly, there remains a need to identify and synthesize a compound with minimized toxicity, providing antiviral activity including, but not limited to, microbicidal activity. There remains a need for a pharmaceutical composition incorporating this compound, and for methods of treatment, inhibition of viral transmission, and elimination of virus in blood, blood products, organs and whole body preparations incorporating this compound.

SUMMARY OF THE INVENTION

The present invention is directed to a new class of compounds, methods for their synthesis, and to the use of these compounds in providing antiviral activity. This class of compounds is produced by alkylsulfation (alkylsulfonation) and sulfation (sulfonation) of dextrin or dextran. The reaction used introduces aliphatic alkyl groups and sulfur groups onto a carbohydrate or polysaccharide. This reaction randomly replaces the reactive hydrogen atoms with a methylsulfate group or a sulfate group and allows for a combinatorial production of sulfate and methylsulfate substitution of dextrin or dextran. The variables of this reaction that can be controlled include the choice of dextrin or dextran as a reactant, the polymeric size of the starting material, the degree of total methylsulfation and sulfation, the degree of methylsulfation and sulfation per saccharide, and position of methylsulfation and sulfation (sulfonation) and the character of the counter ion. Control of these variables, along with the polymeric size of the starting material and degree of hydrolysis during the reaction or work-up, produces a wide range of polymeric compounds. These new compounds are distinctly different from other compounds introduced for anti-HIV therapy. These compounds have a unique synthesis, unique chemical properties and a unique pattern of activity against HIV. Use of these compounds overcomes the absorption obstacles, toxicity obstacles, and efficacy obstacles presented by prior art compounds while retaining the anti-HIV properties of sulfated saccharides. Use of the compounds of the present invention, incorporating alkyl sulfonate groups, embodies the realization that these obstacles are related to the linear sulfated structures and the non-attenuated high degree of anionicity characteristic of these sulfated compounds, and the lack of the presence of an inhibitor to enzymatic sulfate hydrolysis.

The invention introduces four important changes. First, the crucial structural element required for anti-HIV activity is recognized to be the cluster of sulfate groups presented on the branch point structures. Second, the structural element of toxic side effects is recognized as the sulfate groups on the linear portions. Elimination of linear portions and amplification of branch point sulfated structures decreases toxic side effects and increases therapeutic effects. Third, introduction of the methylsulfate group in synergy with the sulfate group increases efficacy by several possible mechanisms, including the providing of an inhibitor to sulfate hydrolyzing enzymes, the attenuation of the large negative charge and the proposed increase in oral, systemic and cellular absorption and efficacy. Finally, the number of sulfated structures or combinations of structures provides variable sites for binding and enzyme inhibition.

The antiviral activity of the compounds of the present invention is explained here in relation to, but is not limited to, the Human Immunodeficiency Virus (HIV). The generally accepted theory is that Acquired Immunodeficiency Disease Syndrome (AIDS) is caused by the Human Immunodeficiency Virus (HIV) and that the prevention of the reproduction of HIV will prevent AIDS. The reproduction of the virus relies on the function of the reverse transcriptase enzyme (RT). RT function requires the binding protein Trans Activating Transcriptor (TAT). The present invention prevents the reproduction of HIV by binding with the TAT protein and preventing the proper function of RT.

The comparatively low toxicity and comparative absence of detrimental effects on body tissue allow the use of the compounds of the present invention in a number of applications calling for compounds exhibiting antiviral activity. The compounds may be used directly, alone or in combination with other therapy, as an antiviral or anti-HIV drug. The compounds of the present invention may also be used in preventative treatments for HIV or other viruses. Routes of administration for these uses include oral and topical administration, and sub-cutaneous, muscular, intraperitoneal or intravenous injection. The compounds of the present invention may be used in bound and unbound form to eliminate HIV or other viruses from blood products during dialysis of organ or whole body preparations. They may also be used alone or in combination in cell culture systems or organ preservation systems to destroy or prevent HIV or other viral growth.

BRIEF DESCRIPTION OF THE DRAWINGS

FIG. 1 is a pictorial illustration of dextrin;

FIG. 2 is a pictorial illustration of a limit dextran;

FIG. 3 is one exemplary chemical structure for polysulfated polymethylsulfated dextrin;

FIG. 4 shows Structure 1 of a polysulfated polymethylsulfated dextrin compound linked to a branch point glucose molecule with an α1→6 linkage;

FIG. 5 shows Structure 2 of a polysulfated polymethylsulfated dextrin compound linked to a branch point maltose molecule with an α1→6 linkage;

FIG. 6 shows Structure 3 of a polysulfated polymethylsulfated dextrin compound linked to a branch point maltose molecule with an α1→6 linkage and linked to a branch point glucose molecule with an α1→4 linkage;

FIG. 7 shows Structure 4 shows a polysulfated polymethylsulfated dextrin compound linked to a branch point glucose molecule with an α1→6 linkage and linked to a branch point glucose molecule with an α1→4 linkage;

Table 1 lists the various chemical moieties that can be substituted on carbons 2-4 and 6 of the different glucose molecules for Structure 1;

Table 2 lists the various chemical moieties that can be substituted on carbons 2-4 and 6 of the different glucose molecules for Structure 2;

Table 3 lists the various chemical moieties that can be substituted on carbons 2-4 and 6 of the different glucose molecules for Structure 3;

Table 4 lists the various chemical moieties that can be substituted on carbons 2-4 and 6 of the different glucose molecules for Structure 4; and Table 5 shows the resulting p24 values (pg/ml) as a measurement of HIV concentration for the indicated concentrations of three separate efficacy tests.

DESCRIPTION OF THE PREFERRED EMBODIMENTS

The starting material for synthesis of the product of the present invention is common corn starch or dextrin, pictorially illustrated in FIG. 1. Dextrin is chemically characterized as a glucose polymer. The polymer consists of linear chains having glucose units linked with alpha (1-4) glycocidic bonds. Multiple linear chains are linked with alpha (1-6) glycosidic bonds along the length of any other given linear chain. The resulting structure increases in size as more glucose molecules are added increasing the length of the linear chains and increasing the number of the branches. The group of glucose molecules having both alpha (1-4) and alpha (1-6) glycosidic bonds is termed the branch point or branch point structure.

Degradation of the starting dextrin with enzymes has been discussed in the scientific literature. The process involves treatment of the dextrin with starch-digesting enzymes called amylases. Beta-amylase is an exo-glycosidase which hydrolyzes polysaccharides at alpha-(1-4) links from the non-reducing end liberating two glucose units or maltose. The cleavage continues until the enzyme encounters an alpha-(1-6) link and then stops. The branch point glucose molecules will have either none or one glucose molecule remaining attached to each of the exposed non-reducing number four carbons. This resulting highly branched starch molecule is called a beta-limit dextrin. Alpha-amylase is an endo-glycosidase which hydrolyzes polysaccharides at alpha-(1-4) links from the reducing end. The enzyme requires a polymer of seven glucose molecules to attach so the next glucose molecule can be cleaved. The alpha-amylase will not hydrolyze alpha-(1-6) links and has decreased activity at alpha-(1-4) links located next to the alpha-(1-6) links. However, the hydrolysis will occur between two neighboring alpha-(1-6) branch points if the required number of seven alpha-(1-4) links are present. Branch points are separated by about twenty-five glucose molecules in starch amylopectin. Hydrolysis by alpha-amylase would result in a branch point with short linear portions of seven to twenty-five glucose molecules attached to the non-reducing carbon number four of the branch point glucose molecules and a glucose polymer of zero to eighteen (that is 25 minus 7) glucose molecules attached to the reducing carbon one of the branch point glucose. This resulting collection of molecules is called an alpha-limit dextrin. A representative pictorial illustration of a limit dextran is shown in FIG. 2.

Exhaustive enzymolysis of the starch results in the production of pure branch points or branch points with short linear segments of glucose alpha-(1-4) polymers attached to the branch point. The branch point structures vary by the number of glucose units and availability of substitution position. As a result of the processes which produce the branch point structures, the number of glucose units at the non-reducing end of the branch point will be necessarily very short and contain either no extra glucose units or one unit in the most commonly occurring situation, two glucose units as the next most common situation and three glucose units in the least likely situation. The presence of four or more glucose units at the non-reducing end of the branch point indicates incomplete reaction hydrolysis. The length of glucose linear polymer at the reducing end of the branch point will range from no extra glucose units to seven glucose units in the most commonly occurring situation. Chain lengths of eight to eighteen glucose units are possible but the abundance falls as the length increases. The most preferred branch points have either none or one extra glucose molecule at either of the non-reducing branch point carbon four positions and a short polymer of eight or less glucose molecules at the reducing carbon one of the branch point. A third method of obtaining branch point structures, discussed in the scientific literature, is to synthesize the branch point structures from individual glucose units.

There are two possible synthetic paths to obtain the branch point polysulfated polymethylsulfated dextrin product starting with dextrin. The first path involves enzymatic or chemical degradation of the starting material dextrin into a structure which will expose the branch point structures followed by chemical replacement of the hydroxyl groups with sulfate and methylsulfate groups. The second path involves chemical replacement of the hydroxyl groups with sulfate and methylsulfate groups as the first step, followed by enzymatic or chemical degradation to eliminate non-branch point structures.

Chemical replacement of the hydroxyl groups with charged sulfate groups and non-charged methylsulfate groups is performed by a simultaneous competitive reaction of reagents such as chlorosulfonic acid, methylchlorolsulfonate, and a sulfurtrioxide pyridine complex on the limit dextrin or branch point structure starting material. This chemical replacement, however, can be performed in two individual steps. Also, there are changes that can be made in the choice of reagent or solvent. These changes may alter the purification techniques required to obtain end product suitable for use in clinical studies.

The total sulfate composition of the polysulfate polymethysulfate dextrin is about 12 to 21 percent sulfation. It is proposed that, because of the increased reactivity of the sulfation reagent over the methylsulfation reagent, the ratio of sulfate to methylsulfate will favor sulfate by about 2 to 1. It is also proposed that the exposed or primary branch point carbon groups will have the highest degree of sulfation. The secondary branch points, defined as the second branch from the exposed surface, react at a decreased rate and are less sulfated. Position 6 is the most exposed and the most highly susceptible to substitution. Position 2 and position 3 are the least likely for sulfate substitution and would be expected to be present in a low proportion. Position 4, if hydrolyzed, has a high probability of substitution.

To obtain active product with the least number of side effects the length of linear chains should be minimized and the number of sulfate and methylsulfate groups should be minimized. As the parameters are limited the potency of the drug may decrease. The potency of sulfated polysaccharides has been shown to be related to the degree of sulfation and size of the polymer. The minimum number of glucose units with strategically located methylsulfate and sulfate groups is the most preferred. For example, one methylsulfate group located at the carbon-6 position of the leading glucose unit and one sulfate group at the carbon-2 position of the base glucose of the branchpoint is a preferred arrangement.

The synthetic strategy is to ultimately obtain a collection of branch point structures with varying amounts of combinatorial chemical alteration. The chemical alteration is the replacement of the hydroxyl groups of the individual glucose molecules in the branch point structure with either a negatively charged sulfate groups accompanied with a suitable counter ion or a non-charged methylsulfate group. The number of possible differing chemical structures is large and is calculated from the variability of the branch point structure, the number of charged versus non-charged sulfate groups on a particular branch point structure, the position of the charged versus non-charged groups on the branch point structure, and the nature of the counter ions. FIG. 3 shows one exemplary chemical structure for the polysulfated polymethysulfated dextrin compound of the present invention. FIGS. 4-7 show four polysulfated polymethylsulfated dextrin compounds, each one differing in their branch point structures. For example, Structure 1 is a polysulfated polymethylsulfated dextrin compound linked to a branch point glucose molecule with an $\alpha 1 \rightarrow 6$ linkage, as shown in FIG. 4. Structure 2 is a polysulfated polymethylsulfated dextrin compound linked to a branch point maltose molecule with an $\alpha 1 \rightarrow 6$ linkage, as shown in FIG. 5. Structure 3 is a polysulfated polymethylsulfated dextrin compound linked to a branch point maltose molecule with an $\alpha 1 \rightarrow 6$ linkage and linked to a branch point glucose molecule with an $\alpha 1 \rightarrow 4$ linkage, as shown in FIG. 6. Structure 4 is a polysulfated polymethylsulfated dextrin compound linked to a branch point glucose molecule with an $\alpha 1 \rightarrow 6$ linkage and linked to a branch point glucose molecule with an $\alpha 1 \rightarrow 4$ linkage, as shown in FIG. 7. Tables 1-4 list the various chemical moieties that can be substituted on carbons 2-4 and 6 of the different glucose molecules for Structures 1-4, respectively.

Applicant believes, without wishing to be bound by the statement, that the alkylsulfate of limit dextrin contributes to the activity of the alkyl sulfate of sulfated dextrin of the present invention.

The methylsulfate group and other alkylsulfate groups, such as ethylsulfate or propylsulfate groups, may also be added to any other sulfates that have been tested for antiviral activity, such as cyclodextrin sulfate and other non-polymeric structures. The resulting compounds include saccharides containing both sulfate and alkylsulfate groups. Dextrin, dextran and cyclodextrin may serve as the saccharides.

Numerous mechanisms of action have been proposed for the observed anti-HIV activity of the sulfated saccharides. These previously proposed mechanisms of actions support the demonstrated anti-HIV activity of the invention. In addition, unique mechanisms of action are proposed to explain the function of the invention.

The large and highly negatively charged polymeric polysulfates are not believed to be capable of entering the cell. The mechanism of action of these large sulfates involve processes at the surface of the cell. These include the prevention of viral absorption into the cell or prevention of budding of the reproduced virus from the cell. As opposed to the linear binding array as represented by dextran sulfate and curdlan sulfate, the invention places the proposed active branch points, or alpha 1-6 gycosidic linkages, on the surface of the molecule creating a three dimensional surface which enhances the binding the invention and the proteins at the cell surface.

However, in the cellular based testing results presented of the proposed compound, the virus was first placed in the cell before addition of the test compound. Therefore, because the virus was already in the cell, reproduction within the cell did not depend on entry. If the test compound simply prevented the HIV particle from entering the cell then it should show no activity in this type of assay. This is evidence that the mechanism of action is intracellular which is different from the known mechanism of action of dextran sulfate.

Binding to internal enzymes of the virus has to be considered as a possible mechanism. Experiments with HIV inhibition demonstrate that viral reproduction is inhibited by intracellular mechanisms. The route of absorption of a compound of the present invention may be enhanced because of the lipophilic characteristics of the methylsulfate group. This lipophilic characteristic of the compound may shield the electrostatic repulsion between the compound and the outer wall of the cell so that the compound can pass into the interior of the cell. Inhibition of intracellular reverse transcriptase or protease enzymes is known to effectively inhibit viral reproduction. Other enzymes may also be effected.

The TAT protein is a unique protein in that it plays both an extracellular and intracellular role in viral reproduction. TAT binds with RT to allow accelerated DNA synthesis and is thought to be the reason for the great increase in viral load during active infection. This protein is manufactured in large numbers and is released from the infected cell. The TAT protein then enters uninfected cells awaiting the arrival of the virus. Once infected, the newly functioning RT is able to immediately function at the accelerated level. The binding of the sulfate group to an active site arginine on the TAT protein is proposed to be the mechanism of inhibition. This proposed mechanism would explain the ability of the invention to prevent systemic viral conversion during the initial periods of infection.

The polysulfated polymethysulfate exhibits an increased antiviral activity in comparison to dextrin sulfate. A proposed explanation is that the high concentrations of enzymes in the white blood cells called sulfatases, which hydrolyze the sulfate group, inactivates polysulfated compounds. The polymethylsulfate derivative of polysulfate dextrin retains activity, possibly because the methylsulfate moiety acts as an inhibitor of the sulfatase enzyme. This prevents drug decomposition or deactivation.

A number of routes of administration are suitable for the compounds of the present invention. These compounds are included, for therapeutic evaluation, in antiviral compositions containing excipients appropriate to the route of administration. The route of administration of a drug may be oral, topical, intra-peritoneal/-muscular/-cutaneous or intravenous. The route used depends on the ability to achieve therapeutic results along with minimization of side effects and eventually compliance. As a drug of the nature of the drug of the present invention is developed, the optimum goal is to develop an oral dosing medication.

The early stage of testing may find success in either topical mucosal application or intravenous route of administration. These routes of delivery are chosen because they eliminate or minimize many of the variables of absorption, distribution, metabolism and elimination. The topical application places the drug directly on the mucosal membrane. Systemic, side effects can be minimized and local toxic effects can be observed. The therapeutic effect is measured in the population response as decrease in disease rate of spread.

Intravenous administration places the drug directly into the blood. However, toxic effects may be amplified because of this route. To minimize toxic side effects a slow continuous infusion or a multiple bolus dosing can be used. The serum drug concentration is monitored to develop a concentration response curve. The infusion rate or bolus dose and frequency is altered to maintain a drug concentration or to increase levels. The effect or therapeutic benefit is measured by periodic measurement of total viral load and p24 concentration. A common known reversible side effect of polymeric sulfates is an increase in the APTT or bleeding time. Therefore, in tests involving compounds of the present invention, the APTT is monitored and maintained at pre-selected values. The platelet count is also monitored in that thrombocytopenia is a possible expected reversible side effect.

Experimental results indicate that the compounds of the present invention provide unexpected and extended modes of action. Therefore, it is expected that the antiviral activity of the compounds of the present invention is not limited to a single viral agent. Target viruses for the evaluation of prior art antimicrobials include HIV, herpes viruses such as cytomegalovirus and herpes simplex, hepatitis agents, and the papilloma virus. Efficacy of the compounds of the present invention in treatment of these species is therefore not unexpected.

The object of antiviral drug therapy, such as anti-HIV drug therapy, is to produce and maintain a therapeutic response. The response may be as vague as a feeling of improvement or the precise measurement of a parameter such as viral load or serum p24 levels. Attempts have to be made to minimize toxic side effects while achieving the goal of a therapeutic response. Adjustments in the dosing form, amount, dosing interval, adjuvant therapy, supportive chemotherapeutics and expected response window.

Pharmacokinetic parameters relate the amount of drug in the body or serum concentration to desired effect rather than relating the dose amount or dose frequency to the desired effect. However, the practical matter is to first determine the dose amount and frequency which produces the desired effect and then to describe this by determining the drug serum concentration. In-vitro experiments help to describe a rough estimate of concentration of active drug which produces a specific response. In-vitro experiments also demonstrate, on a cellular level, toxicity. The ratio of the concentration which produces a therapeutic response and the concentration which produces a toxic response is termed the therapeutic index.

The goal, however, is to determine the therapeutic concentration in a patient with disease. The goal is to reverse disease. Toxic effects are judged with regard to the therapeutic benefit. The goal is to place in check toxic effects so that the drug concentration can be increased and maintained. A patient population must be studied to overcome the natural variability of response traditionally observed from patient to patient when treating disease. The goal of maintaining a therapeutic response can then be achieved.

EXAMPLES

Example 1

Purification of Dextrin

Type I corn starch dextrin of USP grade having a molecular weight distribution of approximately 30% of 2,000 to 4,000 daltons and 60% of 8,000 to 10,000 daltons as determined by gel permeation chromatography is supplied. The dextrin is purified by dissolving into sufficient purified water and dialyzing against purified water. The dialysis membrane has a pore size of 3000 to 6000 daltons so that smaller size dextrin and impurities are eliminated. The purified starting material is then dried by lyophilization and is obtained as a white fluffy solid, melting point 266-274° C. with decomposition.

Example 2

Synthesis of Polysulfate Polymethylsulfate Dextrin

To 10 mL of dry pyridine is added 1.0 mL of methanesulfonyl chloride and 1.0 mL of chlorosulfonic acid. To this is added 500 mg of dextrin. The mixture is heated to 55° C. for a period of twelve hours. Ten grams of sodium hydroxide in 100 mL of water is then added. The aqueous layer is transferred to a dialysis membrane and dialysed against water until the pH is neutral. The polysulfate polymethylsulfate dextrin is obtained as a fluffy white solid by removal of the water by lyophilization. Weight 455 mg; melting point 185-215 degrees Celsius with decomposition 215-220 degrees Celsius. Elemental analysis shows carbon 31.27%, hydrogen 6.38%, and sulfur 11.28%. The 300 MHZ NMR in deuterium shows a broad singlet at 5.8 to 5.4 ppm and a broad quartet at 4.5 to 3.2 ppm.

The methysulfate group may be added to any other sulfates that have been tested for antiviral activity such as dextrin sulfate, dextran sulfate, cyclo-dextrin sulfate, or other non-polymeric sulfated structures using this reaction.

Example 3

Synthesis and Purification of Polysulfate Polymethylsulfate Dextrin from Sulfated Dextrin To 10 mL of clean dry pyridine is added 1.0 mL of methanesulfonyl chloride. The addition requires stirring and cooling. This mixture is then heated to 55° C. To this is added 500 mg of sulfated dextrin with stirring. The mixture is heated to 55° C. and stirred for a period of twelve hours. The mixture is then cooled and ten grams of cooled sodium hydroxide in 100 mL of water is slowly added with stirring and cooling.

The aqueous layer is allowed to separate and is transferred to a dialysis membrane and dialyzed against purified water until the pH of the water remains neutral. The polysulfate polymethylsulfate dextrin is obtained as a solid by removal of the water by lyophilization.

The above synthesis can be applied to any form of sulfated dextrin such as dextrin-2-sulfate, dextrin-3-sulfate, dextrin-6-sulfate or multiple sulfates. Any molecular weight of sulfate dextrin can be used such as those with a molecular weight of 3000 to 10,000 and higher polymers with a molecular weight of, for example, 10,000 to 500,000.

Example 4

Synthesis of Polysulfate Polymethylsulfate Dextrin with Sulfurtrioxide Pyridine Complex and Purification Thereof (a) Production of the Solid Product: 300 mL of dry pyridine is added to a reaction flask heated to 20° C. 120 mL of chlorosulfonic acid is slowly added to the flask, keeping the temperature no higher than 20° C. 120 mL of methanesulfonyl chloride is added over 15 minutes, keeping the temperature below 30° C. Another 300 mL pyridine is added to the mixture, and then 95 g of sulfurtrioxide pyridine complex ($PySO_3$) is added, keeping the temperature below 40° C. The presence of any solids is determined and then the mixture is heated to 55-60° C. If a bulk of un-dissolved salts are present in the mixture, then 50 mL of pyridine is added every 2-3 minutes up to a maximum of 300 mL of additional pyridine. When the mixture is homogeneous, 152.93 g of dry dextrin is stirred into the mixture and the mixture is heated to between 55-60° C. for one hour. After one hour, the mixture is cooled and stirred overnight at room temperature. The final product is a solid. The pyridine is decanted from the solids and retained. Then the solids then are removed using a first wash solution, described below. The solids are filtered using a Buchner funnel and Whatner filter paper # 4. To assist drying of the solids, a latex sheet can be placed over the solids in the Buchner funnel during the filtration process. The solid product then is washed with two wash solutions in the following order: The first wash is made up of ice cold 97.5% acetone and 2.5% HCl (v/v). The volume of this wash should be approximately 500-1000 mL. This removes most of the pyridine and deactivates the remaining reagent. The second wash is made up of about 500 mL ice cold 100% acetone. This removes excess acid.

(b) Neutralization and Purification of the Solid Product: The solid product first is made basic by dissolving it in 10% NaOH. The pH of the solution should be between 10 and 11. The solution then is transferred to a dialysis membrane for dialysis. The amount of base is determined by the pH reading and the amount of water is determined by the dialysis step. A large amount of excess base is not favorable and dialysis limits the amount of water that can be used. Purification of the product is achieved by dialysis against a 1000 MW cut off membrane. The dialysis membrane thus has a smaller pore size than the purification step. Dialysis proceeds with water exchanges until the exchange water pH is neutral, which takes about 72 hours and requires about 6 water changes done about every 6-8 hours. After the exchange water has neutralized, it may be assumed that the product also has a neutral pH. The product then is removed from the dialysis membrane and placed on a lyophilizer for immediate freeze-drying. The water is removed by the freeze-drying method so as not to destroy the product. The polysulfate polymethylsulfate dextrin product is obtained as a slightly acrid, tan solid by removal of the water by lyophilization. Weight: 125 g; pH: 7.5; melting point: 185-215° C. with decomposition at about 215-220° C. Elemental analysis shows carbon: 18.24%; hydrogen: 3.42%; nitrogen: 0.38%; sulfur: 15.91%; and oxygen: 49.45%. Percentage organic matter: 67% (ash: 33%).

Example 5

In vivo Toxicity Study of Polysulfate Polymethylsulfate Dextrin with Sulfurtrioxide Pyridine Complex in Rats (a) Intraperitoneal Administration: Sprague-Dawley rats weighing approximately 250 g were injected i.p. with increasing amounts of polysulfate polymethylsulfate dextrin dissolved in sterile water. The $LD_{50}$, calculated by semi-log plot of the data, was 47 mg/kg body weight.

(b) Oral Administration: Sprague-Dawley rats weighing approximately 250 g were orally gavaged with increasing amounts of polysulfate polymethylsulfate dextrin dissolved in sterile water up to a dose of 2 g/kg body weight. No toxic effects of the compound was observed, thus indicating that oral administration was "non-toxic."

Example 6

Anti-HIV Testing of Polysulfate Polymethylsulfate Dextrin

Anti-HIV activity of polysulfate polymethylsulfate dextrin was demonstrated in cell culture by inhibition of cell-to-cell transmission of the Human Immunodeficiency Virus as measurement of the p24 protein production in the presence of increasing drug concentration. The average of three separate tests demonstrated that the calculated 50% inhibition (IC50) is 1.16 µM. Testing was performed independently at the NIH using standard testing protocol. Results are shown in Table 5.

Example 6

Oral Administration of Antiviral Compound for Treatment of HIV

Oral administration is the most preferred route of administration for general distribution of the invention allowing ease of dose manufacturing and dispensing. Absorption through the gut wall is substantial and adequate because of the increase in lypophilic character of the methylsulfate groups compared to the sulfate groups alone. The decrease in molecular weight by elimination of the linear polymer connecting the branch point structure also increases transport across the gut wall as compared to the limit dextrin. Formulation of the invention with solubilizing lipid carriers, buffered excipients, and dissolution enhancers maximizes absorption. The first pass hepatic clearance is expected to be substantial and should be overcome by increasing the oral dose amount and dosing frequency.

Formulation for oral absorption may include any of the following excipients: glycerin USP, microcrystalline cellulose, methylcellulose, starch, paraben, methylparaben, colloidal silicon dioxide, magnesium stearate, simethicone, sorbitol, water, FD&C color, and flavor.

EXAMPLE FORMULATION: 1 gram of antiviral composition of the present invention in a soft gel capsule.

EXAMPLE DOSAGE: 1 capsule four times a day.

PURPOSE: To determine the effectiveness of the antiviral composition of the present invention towards the treatment of HIV as the drug is administered orally.

METHODOLOGY: The study is an open label study. Subjects are given monthly supplies of the medication: The subjects self-administer the medication and make records in a daily journal. The subjects are medically examined monthly, which may include serum blood drug levels, viral titer or anti-body measurement, serum chemistry measurements, and serum bleeding parameters.

Patients take medication at a starting dose which is adjusted on a monthly basis. If the medication is tolerated and the viral load has not decreased, then the medication is increased from 10% to 1000%. If the medication is not tolerated the medication will be decreased 10% to 100%.

INCLUSION CRITERIA: HIV infection as documented by ELISA or EIA and confirmed by a Western blot analysis.

EXCLUSION CRITERIA: Known allergy to the medication.

END POINT: Elimination of HIV infection.

Example 8

Intravenous Administration of Antiviral Compound for Treatment of HIV

Intravenous administration is the most preferred route of administration for initial clinical trials because it ensures that the invention reaches the systemic circulation. Administration is best accomplished through a large catheter in the femoral or sub-clavian vein to avoid the complication of small vein irritation. Dosing protocol is variable to include one time bolus dosing, multiple dosing protocols which vary the amount of the drug and/or the time interval between dosing, or continuous infusion.

Formulation for intravenous administration may contain any of the following excipients: sterile water, saline, phosphate buffer, dextran, and sodium hydroxide.

EXAMPLE FORMULATION: Sterile solution 15 mg/mL "antiviral composition" in 0.9% sodium chloride adjusted to pH 6.0 to 7.5 with 0.01N sodium hydroxide sterilized with a 0.2 µm filter.

EXAMPLE DOSAGE: 100 mg of "antiviral composition" per 24 hour period delivered over a four hour infusion.

PURPOSE: To determine the effectiveness of the invention "antiviral composition" towards the treatment of HIV as the drug is administered intravenously.

METHODOLOGY: The study is an open label study. Subjects are given daily doses of the medication. The medication is given in a medical setting and records in a daily chart are kept. The subjects are medically assessed daily, as need be, which may include serum blood drug levels, viral titer or anti-body measurement, serum chemistry measurements, and serum bleeding parameters.

Patients are administered medication at a starting dose which is adjusted on a daily basis. If the medication is tolerated and the viral load has not decreased then the medication is increased from 10% to 1000%. If the medication is not tolerated the medication is decreased 10% to 100%.

INCLUSION CRITERIA: HIV infection as documented by ELISA or EIA and confirmed by a Western blot analysis.

EXCLUSION CRITERIA: Known allergy to the medication.

END POINT: Elimination of HIV infection.

Example 9

Intraperitoneal Administration of Antiviral Composition for the Treatment of HIV Intraperitoneal administration is the least preferred route of administration used for general use or for initial clinical trials. The benefit of intraperitoneal administration is the possible reduction of systemic toxic side-effects: circulating white blood cells are exposed to the drug invention. The drug invention is formulated in a phosphate buffer, a pH adjusted saline solution, a dextrin solution, a lipid emulsion or a combination.

Formulation for intraperitoneal administration may contain any of the following excipients: sterile water, saline, dextrin, icodextrin, phosphate buffer.

EXAMPLE FORMULATION: 0.015% w/v of "antiviral composition" in 4% icodextrin solution.

EXAMPLE DOSAGE: 100 mg of "antiviral composition" per 24 hour period delivered the intraperitoneal cavity.

PURPOSE: To determine the effectiveness of the invention "antiviral composition" towards the treatment of HIV as the drug is administered intraperitoneally.

METHODOLOGY: The study is an open label study. Subjects are given daily doses of the medication. The medication is given in a medical setting and records in a daily chart are kept. The subjects are medically assessed daily, as need be, which may include serum blood drug levels, viral titer or anti-body measurement, serum chemistry measurements, and serum bleeding parameters.

Patients are administered medication at a starting dose which is adjusted on a daily basis. If the medication is tolerated and the viral load has not decreased then the medication is increased from 10% to 1000%. If the medication is not tolerated the medication is decreased 10% to 100%.

INCLUSION CRITERIA: HIV infection as documented by ELISA or EIA and confirmed by a Western blot analysis.

EXCLUSION CRITERIA: Known allergy to the medication.

END POINT: Elimination of HIV infection.

Example 9

Topical Administration of Antiviral Composition for Prevention of HIV

Topical administration is a possible preferred route of administration for initial clinical trials because it may eliminate systemic absorption difficulties and toxicities. Administration is controlled by the subject; the formulation is self-administered. Dosing protocol is variable to include one time bolus dosing as well as multiple dosing protocols which vary the amount of the drug and/or the time interval between dosing.

Formulation for topical administration may contain any of the following excipients: petroleum jelly, petroleum ointment mixture, sterile water, saline, phosphate buffer, and dextran.

EXAMPLE FORMULATION: 0.1% ointment; petroleum based ointment with a pH buffer of 6.8.

EXAMPLE DOSAGE: 0.5 gram of ointment within one hour before and one hour after intercourse to vaginal mucosa.

PURPOSE: To determine the effectiveness of the invention "antiviral composition" towards the prevention of HIV as the drug is administered topically.

METHODOLOGY: The study is an open label study. The study population contains 1000 females who are sexually active with a high risk male population. A known population transmission rate or an untreated group may act as controls. Subjects are given a supply of individual doses of the medication. The medication is self-administered. The subjects are medically assessed weekly, as need be, which may include physical and pelvic examination, serum blood drug levels, viral titer or anti-body measurement, serum chemistry measurements, and serum bleeding parameters.

Patients are administered medication at a starting dose which is adjusted on a daily basis. If the medication is tolerated and the viral load has not decreased then the medication is increased from 10% to 1000%. If the medication is not tolerated the medication is decreased 10% to 100%.

INCLUSION CRITERIA: Free of HIV infection as documented by ELISA or EIA.

EXCLUSION CRITERIA: Presence of HIV infection and known allergy to the medication.

END POINT: Presence of acquired HIV infection.

The above invention has been described with reference to the preferred embodiment. Other modifications and alterations will occur to others upon reading and understanding the preceding detailed description. It is intended that the invention be construed as including all such modifications and alterations insofar as they come within the scope of the appended claims or the equivalents thereof.

TABLE 1

Various chemical moieties for Structure 1.
COMBINATIONS FOR STRUCTURE 1

| | 2<br>A, E or H | 3<br>B, F or I | 4<br>C or G | 6<br>D or J | 1<br>K |
|---|---|---|---|---|---|
| 1 | SO2Me | SO2Me | SO2Me | SO2Me | POLYMER |
| 2 | SO2Me | SO2Me | SO2Me | SO3—X+ | POLYMER |
| 3 | SO2Me | SO2Me | SO2Me | H | POLYMER |
| 4 | SO2Me | SO2Me | SO3—X+ | SO2Me | POLYMER |
| 5 | SO2Me | SO2Me | SO3—X+ | SO3—X+ | POLYMER |
| 6 | SO2Me | SO2Me | SO3—X+ | H | POLYMER |
| 7 | SO2Me | SO2Me | H | SO2Me | POLYMER |
| 8 | SO2Me | SO2Me | H | SO3—X+ | POLYMER |
| 9 | SO2Me | SO2Me | H | H | POLYMER |
| 10 | SO2Me | SO3—X+ | SO2Me | SO2Me | POLYMER |
| 11 | SO2Me | SO3—X+ | SO2Me | SO3—X+ | POLYMER |
| 12 | SO2Me | SO3—X+ | SO2Me | H | POLYMER |
| 13 | SO2Me | SO3—X+ | SO3—X+ | SO2Me | POLYMER |
| 14 | SO2Me | SO3—X+ | SO3—X+ | SO3—X+ | POLYMER |
| 15 | SO2Me | SO3—X+ | SO3—X+ | H | POLYMER |
| 16 | SO2Me | SO3—X+ | H | SO2Me | POLYMER |
| 17 | SO2Me | SO3—X+ | H | SO3—X+ | POLYMER |
| 18 | SO2Me | SO3—X+ | H | H | POLYMER |
| 19 | SO2Me | H | SO2Me | SO2Me | POLYMER |
| 20 | SO2Me | H | SO2Me | SO3—X+ | POLYMER |
| 21 | SO2Me | H | SO2Me | H | POLYMER |
| 22 | SO2Me | H | SO3—X+ | SO2Me | POLYMER |
| 23 | SO2Me | H | SO3—X+ | SO3—X+ | POLYMER |
| 24 | SO2Me | H | SO3—X+ | H | POLYMER |
| 25 | SO2Me | H | H | SO2Me | POLYMER |
| 26 | SO2Me | H | H | SO3—X+ | POLYMER |
| 27 | SO2Me | H | H | H | POLYMER |
| 28 | SO3—X+ | SO2Me | SO2Me | SO2Me | POLYMER |
| 29 | SO3—X+ | SO2Me | SO2Me | SO3—X+ | POLYMER |
| 30 | SO3—X+ | SO2Me | SO2Me | H | POLYMER |
| 31 | SO3—X+ | SO2Me | SO3—X+ | SO2Me | POLYMER |
| 32 | SO3—X+ | SO2Me | SO3—X+ | SO3—X+ | POLYMER |
| 33 | SO3—X+ | SO2Me | SO3—X+ | H | POLYMER |
| 34 | SO3—X+ | SO2Me | H | SO2Me | POLYMER |
| 35 | SO3—X+ | SO2Me | H | SO3—X+ | POLYMER |
| 36 | SO3—X+ | SO2Me | H | H | POLYMER |
| 37 | SO3—X+ | SO3—X+ | SO2Me | SO2Me | POLYMER |
| 38 | SO3—X+ | SO3—X+ | SO2Me | SO3—X+ | POLYMER |
| 39 | SO3—X+ | SO3—X+ | SO2Me | H | POLYMER |
| 40 | SO3—X+ | SO3—X+ | SO3—X+ | SO2Me | POLYMER |
| 41 | SO3—X+ | SO3—X+ | SO3—X+ | SO3—X+ | POLYMER |
| 42 | SO3—X+ | SO3—X+ | SO3—X+ | H | POLYMER |
| 43 | SO3—X+ | SO3—X+ | H | SO2Me | POLYMER |
| 44 | SO3—X+ | SO3—X+ | H | SO3—X+ | POLYMER |
| 45 | SO3—X+ | SO3—X+ | H | H | POLYMER |
| 46 | SO3—X+ | H | SO2Me | SO2Me | POLYMER |
| 47 | SO3—X+ | H | SO2Me | SO3—X+ | POLYMER |
| 48 | SO3—X+ | H | SO2Me | H | POLYMER |
| 49 | SO3—X+ | H | SO3—X+ | SO2Me | POLYMER |
| 50 | SO3—X+ | H | SO3—X+ | SO3—X+ | POLYMER |
| 51 | SO3—X+ | H | SO3—X+ | H | POLYMER |
| 52 | SO3—X+ | H | H | SO2Me | POLYMER |
| 53 | SO3—X+ | H | H | SO3—X+ | POLYMER |
| 54 | SO3—X+ | H | H | H | POLYMER |
| 55 | H | SO2Me | SO2Me | SO2Me | POLYMER |
| 56 | H | SO2Me | SO2Me | SO3—X+ | POLYMER |
| 57 | H | SO2Me | SO2Me | H | POLYMER |
| 58 | H | SO2Me | SO3—X+ | SO2Me | POLYMER |
| 59 | H | SO2Me | SO3—X+ | SO3—X+ | POLYMER |
| 60 | H | SO2Me | SO3—X+ | H | POLYMER |
| 61 | H | SO2Me | H | SO2Me | POLYMER |
| 62 | H | SO2Me | H | SO3—X+ | POLYMER |
| 63 | H | SO2Me | H | H | POLYMER |
| 64 | H | SO3—X+ | SO2Me | SO2Me | POLYMER |
| 65 | H | SO3—X+ | SO2Me | SO3—X+ | POLYMER |
| 66 | H | SO3—X+ | SO2Me | H | POLYMER |
| 67 | H | SO3—X+ | SO3—X+ | SO2Me | POLYMER |
| 68 | H | SO3—X+ | SO3—X+ | SO3—X+ | POLYMER |
| 69 | H | SO3—X+ | SO3—X+ | H | POLYMER |
| 70 | H | SO3—X+ | H | SO2Me | POLYMER |
| 71 | H | SO3—X+ | H | SO3—X+ | POLYMER |
| 72 | H | SO3—X+ | H | H | POLYMER |
| 73 | H | H | SO2Me | SO2Me | POLYMER |
| 74 | H | H | SO2Me | SO3—X+ | POLYMER |
| 75 | H | H | SO2Me | H | POLYMER |
| 76 | H | H | SO3—X+ | SO2Me | POLYMER |
| 77 | H | H | SO3—X+ | SO3—X+ | POLYMER |
| 78 | H | H | SO3—X+ | H | POLYMER |
| 79 | H | H | H | SO2Me | POLYMER |
| 80 | H | H | H | SO3—X+ | POLYMER |
| 81 | H | H | H | H | POLYMER |
| 82 | SO2Me | SO2Me | SO2Me | SO2Me | POLYMER |
| 83 | SO2Me | SO2Me | SO2Me | SO3—X+ | POLYMER |
| 84 | SO2Me | SO2Me | SO2Me | H | POLYMER |
| 85 | SO2Me | SO2Me | SO3—X+ | SO2Me | POLYMER |
| 86 | SO2Me | SO2Me | SO3—X+ | SO3—X+ | POLYMER |
| 87 | SO2Me | SO2Me | SO3—X+ | H | POLYMER |
| 88 | SO2Me | SO2Me | H | SO2Me | POLYMER |
| 89 | SO2Me | SO2Me | H | SO3—X+ | POLYMER |
| 90 | SO2Me | SO2Me | H | H | POLYMER |
| 91 | SO2Me | SO3—X+ | SO2Me | SO2Me | POLYMER |
| 92 | SO2Me | SO3—X+ | SO2Me | SO3—X+ | POLYMER |
| 93 | SO2Me | SO3—X+ | SO2Me | H | POLYMER |
| 94 | SO2Me | SO3—X+ | SO3—X+ | SO2Me | POLYMER |
| 95 | SO2Me | SO3—X+ | SO3—X+ | SO3—X+ | POLYMER |
| 96 | SO2Me | SO3—X+ | SO3—X+ | H | POLYMER |
| 97 | SO2Me | SO3—X+ | H | SO2Me | POLYMER |

TABLE 1-continued

Various chemical moieties for Structure 1.
COMBINATIONS FOR STRUCTURE 1

| | 2<br>A, E or H | 3<br>B, F or I | 4<br>C or G | 6<br>D or J | 1<br>K |
|---|---|---|---|---|---|
| 98 | SO2Me | SO3—X+ | H | SO3—X+ | POLYMER |
| 99 | SO2Me | SO3—X+ | H | H | POLYMER |
| 100 | SO2Me | H | SO2Me | SO2Me | POLYMER |
| 101 | SO2Me | H | SO2Me | SO3—X+ | POLYMER |
| 102 | SO2Me | H | SO2Me | H | POLYMER |
| 103 | SO2Me | H | SO3—X+ | SO2Me | POLYMER |
| 104 | SO2Me | H | SO3—X+ | SO3—X+ | POLYMER |
| 105 | SO2Me | H | SO3—X+ | H | POLYMER |
| 106 | SO2Me | H | H | SO2Me | POLYMER |
| 107 | SO2Me | H | H | SO3—X+ | POLYMER |
| 108 | SO2Me | H | H | H | POLYMER |
| 109 | SO3—X+ | SO2Me | SO2Me | SO2Me | POLYMER |
| 110 | SO3—X+ | SO2Me | SO2Me | SO3—X+ | POLYMER |
| 111 | SO3—X+ | SO2Me | SO2Me | H | POLYMER |
| 112 | SO3—X+ | SO2Me | SO3—X+ | SO2Me | POLYMER |
| 113 | SO3—X+ | SO2Me | SO3—X+ | SO3—X+ | POLYMER |
| 114 | SO3—X+ | SO2Me | SO3—X+ | H | POLYMER |
| 115 | SO3—X+ | SO2Me | H | SO2Me | POLYMER |
| 116 | SO3—X+ | SO2Me | H | SO3—X+ | POLYMER |
| 117 | SO3—X+ | SO2Me | H | H | POLYMER |
| 118 | SO3—X+ | SO3—X+ | SO2Me | SO2Me | POLYMER |
| 119 | SO3—X+ | SO3—X+ | SO2Me | SO3—X+ | POLYMER |
| 120 | SO3—X+ | SO3—X+ | SO2Me | H | POLYMER |
| 121 | SO3—X+ | SO3—X+ | SO3—X+ | SO2Me | POLYMER |
| 122 | SO3—X+ | SO3—X+ | SO3—X+ | SO3—X+ | POLYMER |
| 123 | SO3—X+ | SO3—X+ | SO3—X+ | H | POLYMER |
| 124 | SO3—X+ | SO3—X+ | H | SO2Me | POLYMER |
| 125 | SO3—X+ | SO3—X+ | H | SO3—X+ | POLYMER |
| 126 | SO3—X+ | SO3—X+ | H | H | POLYMER |
| 127 | SO3—X+ | H | SO2Me | SO2Me | POLYMER |
| 128 | SO3—X+ | H | SO2Me | SO3—X+ | POLYMER |
| 129 | SO3—X+ | H | SO2Me | H | POLYMER |
| 130 | SO3—X+ | H | SO3—X+ | SO2Me | POLYMER |
| 131 | SO3—X+ | H | SO3—X+ | SO3—X+ | POLYMER |
| 132 | SO3—X+ | H | SO3—X+ | H | POLYMER |
| 133 | SO3—X+ | H | H | SO2Me | POLYMER |
| 134 | SO3—X+ | H | H | SO3—X+ | POLYMER |
| 135 | SO3—X+ | H | H | H | POLYMER |
| 136 | H | SO2Me | SO2Me | SO2Me | POLYMER |
| 137 | H | SO2Me | SO2Me | SO3—X+ | POLYMER |
| 138 | H | SO2Me | SO2Me | H | POLYMER |
| 139 | H | SO2Me | SO3—X+ | SO2Me | POLYMER |
| 140 | H | SO2Me | SO3—X+ | SO3—X+ | POLYMER |
| 141 | H | SO2Me | SO3—X+ | H | POLYMER |
| 142 | H | SO2Me | H | SO2Me | POLYMER |
| 143 | H | SO2Me | H | SO3—X+ | POLYMER |
| 144 | H | SO2Me | H | H | POLYMER |
| 145 | H | SO3—X+ | SO2Me | SO2Me | POLYMER |
| 146 | H | SO3—X+ | SO2Me | SO3—X+ | POLYMER |
| 147 | H | SO3—X+ | SO2Me | H | POLYMER |
| 148 | H | SO3—X+ | SO3—X+ | SO2Me | POLYMER |
| 149 | H | SO3—X+ | SO3—X+ | SO3—X+ | POLYMER |
| 150 | H | SO3—X+ | SO3—X+ | H | POLYMER |
| 151 | H | SO3—X+ | H | SO2Me | POLYMER |
| 152 | H | SO3—X+ | H | SO3—X+ | POLYMER |
| 153 | H | SO3—X+ | H | H | POLYMER |
| 154 | H | H | SO2Me | SO2Me | POLYMER |
| 155 | H | H | SO2Me | SO3—X+ | POLYMER |
| 156 | H | H | SO2Me | H | POLYMER |
| 157 | H | H | SO3—X+ | SO2Me | POLYMER |
| 158 | H | H | SO3—X+ | SO3—X+ | POLYMER |
| 159 | H | H | SO3—X+ | H | POLYMER |
| 160 | H | H | H | SO2Me | POLYMER |
| 161 | H | H | H | SO3—X+ | POLYMER |
| 162 | H | H | H | H | POLYMER |
| 163 | SO2Me | SO2Me | SO2Me | SO2Me | POLYMER |
| 164 | SO2Me | SO2Me | SO2Me | SO3—X+ | POLYMER |
| 165 | SO2Me | SO2Me | SO2Me | H | POLYMER |
| 166 | SO2Me | SO2Me | SO3—X+ | SO3—X+ | POLYMER |
| 167 | SO2Me | SO2Me | SO3—X+ | SO3—X+ | POLYMER |
| 168 | SO2Me | SO2Me | SO3—X+ | H | POLYMER |
| 169 | SO2Me | SO2Me | H | SO2Me | POLYMER |
| 170 | SO2Me | SO2Me | H | SO3—X+ | POLYMER |
| 171 | SO2Me | SO2Me | H | H | POLYMER |
| 172 | SO2Me | SO3—X+ | SO2Me | SO2Me | POLYMER |
| 173 | SO2Me | SO3—X+ | SO2Me | SO3—X+ | POLYMER |
| 174 | SO2Me | SO3—X+ | SO2Me | H | POLYMER |
| 175 | SO2Me | SO3—X+ | SO3—X+ | SO2Me | POLYMER |
| 176 | SO2Me | SO3—X+ | SO3—X+ | SO3—X+ | POLYMER |
| 177 | SO2Me | SO3—X+ | SO3—X+ | H | POLYMER |
| 178 | SO2Me | SO3—X+ | H | SO2Me | POLYMER |
| 179 | SO2Me | SO3—X+ | H | SO3—X+ | POLYMER |
| 180 | SO2Me | SO3—X+ | H | H | POLYMER |
| 181 | SO2Me | H | SO2Me | SO2Me | POLYMER |
| 182 | SO2Me | H | SO2Me | SO3—X+ | POLYMER |
| 183 | SO2Me | H | SO2Me | H | POLYMER |
| 184 | SO2Me | H | SO3—X+ | SO2Me | POLYMER |
| 185 | SO2Me | H | SO3—X+ | SO3—X+ | POLYMER |
| 186 | SO2Me | H | SO3—X+ | H | POLYMER |
| 187 | SO2Me | H | H | SO2Me | POLYMER |
| 188 | SO2Me | H | H | SO3—X+ | POLYMER |
| 189 | SO2Me | H | H | H | POLYMER |
| 190 | SO3—X+ | SO2Me | SO2Me | SO2Me | POLYMER |
| 191 | SO3—X+ | SO2Me | SO2Me | SO3—X+ | POLYMER |
| 192 | SO3—X+ | SO2Me | SO2Me | H | POLYMER |
| 193 | SO3—X+ | SO2Me | SO3—X+ | SO2Me | POLYMER |
| 194 | SO3—X+ | SO2Me | SO3—X+ | SO3—X+ | POLYMER |
| 195 | SO3—X+ | SO2Me | SO3—X+ | H | POLYMER |
| 196 | SO3—X+ | SO2Me | H | SO2Me | POLYMER |
| 197 | SO3—X+ | SO2Me | H | SO3—X+ | POLYMER |
| 198 | SO3—X+ | SO2Me | H | H | POLYMER |
| 199 | SO3—X+ | SO3—X+ | SO2Me | SO2Me | POLYMER |
| 200 | SO3—X+ | SO3—X+ | SO2Me | SO3—X+ | POLYMER |
| 201 | SO3—X+ | SO3—X+ | SO2Me | H | POLYMER |
| 202 | SO3—X+ | SO3—X+ | SO3—X+ | SO2Me | POLYMER |
| 203 | SO3—X+ | SO3—X+ | SO3—X+ | SO3—X+ | POLYMER |
| 204 | SO3—X+ | SO3—X+ | SO3—X+ | H | POLYMER |
| 205 | SO3—X+ | SO3—X+ | H | SO2Me | POLYMER |
| 206 | SO3—X+ | SO3—X+ | H | SO3—X+ | POLYMER |
| 207 | SO3—X+ | SO3—X+ | H | H | POLYMER |
| 208 | SO3—X+ | H | SO2Me | SO2Me | POLYMER |
| 209 | SO3—X+ | H | SO2Me | SO3—X+ | POLYMER |
| 210 | SO3—X+ | H | SO2Me | H | POLYMER |
| 211 | SO3—X+ | H | SO3—X+ | SO2Me | POLYMER |
| 212 | SO3—X+ | H | SO3—X+ | SO3—X+ | POLYMER |
| 213 | SO3—X+ | H | SO3—X+ | H | POLYMER |
| 214 | SO3—X+ | H | H | SO2Me | POLYMER |
| 215 | SO3—X+ | H | H | SO3—X+ | POLYMER |
| 216 | SO3—X+ | H | H | H | POLYMER |
| 217 | H | SO2Me | SO2Me | SO2Me | POLYMER |
| 218 | H | SO2Me | SO2Me | SO3—X+ | POLYMER |
| 219 | H | SO2Me | SO2Me | H | POLYMER |
| 220 | H | SO2Me | SO3—X+ | SO2Me | POLYMER |
| 221 | H | SO2Me | SO3—X+ | SO3—X+ | POLYMER |
| 222 | H | SO2Me | SO3—X+ | H | POLYMER |
| 223 | H | SO2Me | H | SO2Me | POLYMER |
| 224 | H | SO2Me | H | SO3—X+ | POLYMER |
| 225 | H | SO2Me | H | H | POLYMER |
| 226 | H | SO3—X+ | SO2Me | SO2Me | POLYMER |
| 227 | H | SO3—X+ | SO2Me | SO3—X+ | POLYMER |
| 228 | H | SO3—X+ | SO2Me | H | POLYMER |
| 229 | H | SO3—X+ | SO3—X+ | SO2Me | POLYMER |
| 230 | H | SO3—X+ | SO3—X+ | SO3—X+ | POLYMER |
| 231 | H | SO3—X+ | SO3—X+ | H | POLYMER |
| 232 | H | SO3—X+ | H | SO2Me | POLYMER |
| 233 | H | SO3—X+ | H | SO3—X+ | POLYMER |
| 234 | H | SO3—X+ | H | H | POLYMER |
| 235 | H | H | SO2Me | SO2Me | POLYMER |
| 236 | H | H | SO2Me | SO3—X+ | POLYMER |
| 237 | H | H | SO2Me | H | POLYMER |
| 238 | H | H | SO3—X+ | SO2Me | POLYMER |
| 239 | H | H | SO3—X+ | SO3—X+ | POLYMER |
| 240 | H | H | SO3—X+ | H | POLYMER |

TABLE 2

Various chemical moieties for Structure 2.
COMBINATIONS FOR STRUCTURE 2

| | 2<br>A, D, H or K | 3<br>B, E, I or L | 4<br>F or J | 6<br>C, G or M | 1<br>N |
|---|---|---|---|---|---|
| 1 | SO2Me | SO2Me | SO2Me | SO2Me | POLYMER |
| 2 | SO2Me | SO2Me | SO2Me | SO3—X+ | POLYMER |
| 3 | SO2Me | SO2Me | SO2Me | H | POLYMER |
| 4 | SO2Me | SO2Me | SO3—X+ | SO2Me | POLYMER |
| 5 | SO2Me | SO2Me | SO3—X+ | SO3—X+ | POLYMER |
| 6 | SO2Me | SO2Me | SO3—X+ | H | POLYMER |
| 7 | SO2Me | SO2Me | H | SO2Me | POLYMER |
| 8 | SO2Me | SO2Me | H | SO3—X+ | POLYMER |
| 9 | SO2Me | SO2Me | H | H | POLYMER |
| 10 | SO2Me | SO3—X+ | SO2Me | SO2Me | POLYMER |
| 11 | SO2Me | SO3—X+ | SO2Me | SO3—X+ | POLYMER |
| 12 | SO2Me | SO3—X+ | SO2Me | H | POLYMER |
| 13 | SO2Me | SO3—X+ | SO3—X+ | SO2Me | POLYMER |
| 14 | SO2Me | SO3—X+ | SO3—X+ | SO3—X+ | POLYMER |
| 15 | SO2Me | SO3—X+ | SO3—X+ | H | POLYMER |
| 16 | SO2Me | SO3—X+ | H | SO2Me | POLYMER |
| 17 | SO2Me | SO3—X+ | H | SO3—X+ | POLYMER |
| 18 | SO2Me | SO3—X+ | H | H | POLYMER |
| 19 | SO2Me | H | SO2Me | SO2Me | POLYMER |
| 20 | SO2Me | H | SO2Me | SO3—X+ | POLYMER |
| 21 | SO2Me | H | SO2Me | H | POLYMER |
| 22 | SO2Me | H | SO3—X+ | SO2Me | POLYMER |
| 23 | SO2Me | H | SO3—X+ | SO3—X+ | POLYMER |
| 24 | SO2Me | H | SO3—X+ | H | POLYMER |
| 25 | SO2Me | H | H | SO2Me | POLYMER |
| 26 | SO2Me | H | H | SO3—X+ | POLYMER |
| 27 | SO2Me | H | H | H | POLYMER |
| 28 | SO3—X+ | SO2Me | SO2Me | SO2Me | POLYMER |
| 29 | SO3—X+ | SO2Me | SO2Me | SO3—X+ | POLYMER |
| 30 | SO3—X+ | SO2Me | SO2Me | H | POLYMER |
| 31 | SO3—X+ | SO2Me | SO3—X+ | SO2Me | POLYMER |
| 32 | SO3—X+ | SO2Me | SO3—X+ | SO3—X+ | POLYMER |
| 33 | SO3—X+ | SO2Me | SO3—X+ | H | POLYMER |
| 34 | SO3—X+ | SO2Me | H | SO2Me | POLYMER |
| 35 | SO3—X+ | SO2Me | H | SO3—X+ | POLYMER |
| 36 | SO3—X+ | SO2Me | H | H | POLYMER |
| 37 | SO3—X+ | SO3—X+ | SO2Me | SO2Me | POLYMER |
| 38 | SO3—X+ | SO3—X+ | SO2Me | SO3—X+ | POLYMER |
| 39 | SO3—X+ | SO3—X+ | SO2Me | H | POLYMER |
| 40 | SO3—X+ | SO3—X+ | SO3—X+ | SO2Me | POLYMER |
| 41 | SO3—X+ | SO3—X+ | SO3—X+ | SO3—X+ | POLYMER |
| 42 | SO3—X+ | SO3—X+ | SO3—X+ | H | POLYMER |
| 43 | SO3—X+ | SO3—X+ | H | SO2Me | POLYMER |
| 44 | SO3—X+ | SO3—X+ | H | SO3—X+ | POLYMER |
| 45 | SO3—X+ | SO3—X+ | H | H | POLYMER |
| 46 | SO3—X+ | H | SO2Me | SO2Me | POLYMER |
| 47 | SO3—X+ | H | SO2Me | SO3—X+ | POLYMER |
| 48 | SO3—X+ | H | SO2Me | H | POLYMER |
| 49 | SO3—X+ | H | SO3—X+ | SO2Me | POLYMER |
| 50 | SO3—X+ | H | SO3—X+ | SO3—X+ | POLYMER |
| 51 | SO3—X+ | H | SO3—X+ | H | POLYMER |
| 52 | SO3—X+ | H | H | SO2Me | POLYMER |
| 53 | SO3—X+ | H | H | SO3—X+ | POLYMER |
| 54 | SO3—X+ | H | H | H | POLYMER |
| 55 | H | SO2Me | SO2Me | SO2Me | POLYMER |
| 56 | H | SO2Me | SO2Me | SO3—X+ | POLYMER |
| 57 | H | SO2Me | SO2Me | H | POLYMER |
| 58 | H | SO2Me | SO3—X+ | SO2Me | POLYMER |
| 59 | H | SO2Me | SO3—X+ | SO3—X+ | POLYMER |
| 60 | H | SO2Me | SO3—X+ | H | POLYMER |
| 61 | H | SO2Me | H | SO2Me | POLYMER |
| 62 | H | SO2Me | H | SO3—X+ | POLYMER |
| 63 | H | SO2Me | H | H | POLYMER |
| 64 | H | SO3—X+ | SO2Me | SO2Me | POLYMER |
| 65 | H | SO3—X+ | SO2Me | SO3—X+ | POLYMER |
| 66 | H | SO3—X+ | SO2Me | H | POLYMER |
| 67 | H | SO3—X+ | SO3—X+ | SO2Me | POLYMER |
| 68 | H | SO3—X+ | SO3—X+ | SO3—X+ | POLYMER |
| 69 | H | SO3—X+ | SO3—X+ | H | POLYMER |
| 70 | H | SO3—X+ | H | SO2Me | POLYMER |
| 71 | H | SO3—X+ | H | SO3—X+ | POLYMER |
| 72 | H | SO3—X+ | H | H | POLYMER |
| 73 | H | H | SO2Me | SO2Me | POLYMER |
| 74 | H | H | SO2Me | SO3—X+ | POLYMER |
| 75 | H | H | SO2Me | H | POLYMER |
| 76 | H | H | SO3—X+ | SO2Me | POLYMER |
| 77 | H | H | SO3—X+ | SO3—X+ | POLYMER |
| 78 | H | H | SO3—X+ | H | POLYMER |
| 79 | H | H | H | SO2Me | POLYMER |
| 80 | H | H | H | SO3—X+ | POLYMER |
| 81 | H | H | H | H | POLYMER |
| 82 | SO2Me | SO2Me | SO2Me | SO2Me | POLYMER |
| 83 | SO2Me | SO2Me | SO2Me | SO3—X+ | POLYMER |
| 84 | SO2Me | SO2Me | SO2Me | H | POLYMER |
| 85 | SO2Me | SO2Me | SO3—X+ | SO2Me | POLYMER |
| 86 | SO2Me | SO2Me | SO3—X+ | SO3—X+ | POLYMER |
| 87 | SO2Me | SO2Me | SO3—X+ | H | POLYMER |
| 88 | SO2Me | SO2Me | H | SO2Me | POLYMER |
| 89 | SO2Me | SO2Me | H | SO3—X+ | POLYMER |
| 90 | SO2Me | SO2Me | H | H | POLYMER |
| 91 | SO2Me | SO3—X+ | SO2Me | SO2Me | POLYMER |
| 92 | SO2Me | SO3—X+ | SO2Me | SO3—X+ | POLYMER |
| 93 | SO2Me | SO3—X+ | SO2Me | H | POLYMER |
| 94 | SO2Me | SO3—X+ | SO3—X+ | SO2Me | POLYMER |
| 95 | SO2Me | SO3—X+ | SO3—X+ | SO3—X+ | POLYMER |
| 96 | SO2Me | SO3—X+ | SO3—X+ | H | POLYMER |
| 97 | SO2Me | SO3—X+ | H | SO2Me | POLYMER |
| 98 | SO2Me | SO3—X+ | H | SO3—X+ | POLYMER |
| 99 | SO2Me | SO3—X+ | H | H | POLYMER |
| 100 | SO2Me | H | SO2Me | SO2Me | POLYMER |
| 101 | SO2Me | H | SO2Me | SO3—X+ | POLYMER |
| 102 | SO2Me | H | SO2Me | H | POLYMER |
| 103 | SO2Me | H | SO3—X+ | SO2Me | POLYMER |
| 104 | SO2Me | H | SO3—X+ | SO3—X+ | POLYMER |
| 105 | SO2Me | H | SO3—X+ | H | POLYMER |
| 106 | SO2Me | H | H | SO2Me | POLYMER |
| 107 | SO2Me | H | H | SO3—X+ | POLYMER |
| 108 | SO2Me | H | H | H | POLYMER |
| 109 | SO3—X+ | SO2Me | SO2Me | SO2Me | POLYMER |
| 110 | SO3—X+ | SO2Me | SO2Me | SO3—X+ | POLYMER |
| 111 | SO3—X+ | SO2Me | SO2Me | H | POLYMER |
| 112 | SO3—X+ | SO2Me | SO3—X+ | SO2Me | POLYMER |
| 113 | SO3—X+ | SO2Me | SO3—X+ | SO3—X+ | POLYMER |
| 114 | SO3—X+ | SO2Me | SO3—X+ | H | POLYMER |
| 115 | SO3—X+ | SO2Me | H | SO2Me | POLYMER |
| 116 | SO3—X+ | SO2Me | H | SO3—X+ | POLYMER |
| 117 | SO3—X+ | SO2Me | H | H | POLYMER |
| 118 | SO3—X+ | SO3—X+ | SO2Me | SO2Me | POLYMER |
| 119 | SO3—X+ | SO3—X+ | SO2Me | SO3—X+ | POLYMER |
| 120 | SO3—X+ | SO3—X+ | SO2Me | H | POLYMER |
| 121 | SO3—X+ | SO3—X+ | SO3—X+ | SO2Me | POLYMER |
| 122 | SO3—X+ | SO3—X+ | SO3—X+ | SO3—X+ | POLYMER |
| 123 | SO3—X+ | SO3—X+ | SO3—X+ | H | POLYMER |
| 124 | SO3—X+ | SO3—X+ | H | SO2Me | POLYMER |
| 125 | SO3—X+ | SO3—X+ | H | SO3—X+ | POLYMER |
| 126 | SO3—X+ | SO3—X+ | H | H | POLYMER |
| 127 | SO3—X+ | H | SO2Me | SO2Me | POLYMER |
| 128 | SO3—X+ | H | SO2Me | SO3—X+ | POLYMER |
| 129 | SO3—X+ | H | SO2Me | H | POLYMER |
| 130 | SO3—X+ | H | SO3—X+ | SO2Me | POLYMER |
| 131 | SO3—X+ | H | SO3—X+ | SO3—X+ | POLYMER |
| 132 | SO3—X+ | H | SO3—X+ | H | POLYMER |
| 133 | SO3—X+ | H | H | SO2Me | POLYMER |
| 134 | SO3—X+ | H | H | SO3—X+ | POLYMER |
| 135 | SO3—X+ | H | H | H | POLYMER |
| 136 | H | SO2Me | SO2Me | SO2Me | POLYMER |
| 137 | H | SO2Me | SO2Me | SO3—X+ | POLYMER |
| 138 | H | SO2Me | SO2Me | H | POLYMER |
| 139 | H | SO2Me | SO3—X+ | SO2Me | POLYMER |
| 140 | H | SO2Me | SO3—X+ | SO3—X+ | POLYMER |
| 141 | H | SO2Me | SO3—X+ | H | POLYMER |
| 142 | H | SO2Me | H | SO2Me | POLYMER |
| 143 | H | SO2Me | H | SO3—X+ | POLYMER |
| 144 | H | SO2Me | H | H | POLYMER |
| 145 | H | SO3—X+ | SO2Me | SO2Me | POLYMER |
| 146 | H | SO3—X+ | SO2Me | SO3—X+ | POLYMER |
| 147 | H | SO3—X+ | SO2Me | H | POLYMER |
| 148 | H | SO3—X+ | SO3—X+ | SO2Me | POLYMER |

TABLE 2-continued

Various chemical moieties for Structure 2.
COMBINATIONS FOR STRUCTURE 2

| | 2<br>A, D, H or K | 3<br>B, E, I or L | 4<br>F or J | 6<br>C, G or M | 1<br>N |
|---|---|---|---|---|---|
| 149 | H | SO3—X+ | SO3—X+ | SO3—X+ | POLYMER |
| 150 | H | SO3—X+ | SO3—X+ | H | POLYMER |
| 151 | H | SO3—X+ | H | SO2Me | POLYMER |
| 152 | H | SO3—X+ | H | SO3—X+ | POLYMER |
| 153 | H | SO3—X+ | H | H | POLYMER |
| 154 | H | H | SO2Me | SO2Me | POLYMER |
| 155 | H | H | SO2Me | SO3—X+ | POLYMER |
| 156 | H | H | SO2Me | H | POLYMER |
| 157 | H | H | SO3—X+ | SO2Me | POLYMER |
| 158 | H | H | SO3—X+ | SO3—X+ | POLYMER |
| 159 | H | H | SO3—X+ | H | POLYMER |
| 160 | H | H | H | SO2Me | POLYMER |
| 161 | H | H | H | SO3—X+ | POLYMER |
| 162 | H | H | H | H | POLYMER |
| 163 | SO2Me | SO2Me | SO2Me | SO2Me | POLYMER |
| 164 | SO2Me | SO2Me | SO2Me | SO3—X+ | POLYMER |
| 165 | SO2Me | SO2Me | SO2Me | H | POLYMER |
| 166 | SO2Me | SO2Me | SO3—X+ | SO2Me | POLYMER |
| 167 | SO2Me | SO2Me | SO3—X+ | SO3—X+ | POLYMER |
| 168 | SO2Me | SO2Me | SO3—X+ | H | POLYMER |
| 169 | SO2Me | SO2Me | H | SO2Me | POLYMER |
| 170 | SO2Me | SO2Me | H | SO3—X+ | POLYMER |
| 171 | SO2Me | SO2Me | H | H | POLYMER |
| 172 | SO2Me | SO3—X+ | SO2Me | SO2Me | POLYMER |
| 173 | SO2Me | SO3—X+ | SO2Me | SO3—X+ | POLYMER |
| 174 | SO2Me | SO3—X+ | SO2Me | H | POLYMER |
| 175 | SO2Me | SO3—X+ | SO3—X+ | SO2Me | POLYMER |
| 176 | SO2Me | SO3—X+ | SO3—X+ | SO3—X+ | POLYMER |
| 177 | SO2Me | SO3—X+ | SO3—X+ | H | POLYMER |
| 178 | SO2Me | SO3—X+ | H | SO2Me | POLYMER |
| 179 | SO2Me | SO3—X+ | H | SO3—X+ | POLYMER |
| 180 | SO2Me | SO3—X+ | H | H | POLYMER |
| 181 | SO2Me | H | SO2Me | SO2Me | POLYMER |
| 182 | SO2Me | H | SO2Me | SO3—X+ | POLYMER |
| 183 | SO2Me | H | SO2Me | H | POLYMER |
| 184 | SO2Me | H | SO3—X+ | SO2Me | POLYMER |
| 185 | SO2Me | H | SO3—X+ | SO3—X+ | POLYMER |
| 186 | SO2Me | H | SO3—X+ | H | POLYMER |
| 187 | SO2Me | H | H | SO2Me | POLYMER |
| 188 | SO2Me | H | H | SO3—X+ | POLYMER |
| 189 | SO2Me | H | H | H | POLYMER |
| 190 | SO3—X+ | SO2Me | SO2Me | SO2Me | POLYMER |
| 191 | SO3—X+ | SO2Me | SO2Me | SO3—X+ | POLYMER |
| 192 | SO3—X+ | SO2Me | SO2Me | H | POLYMER |
| 193 | SO3—X+ | SO2Me | SO3—X+ | SO2Me | POLYMER |
| 194 | SO3—X+ | SO2Me | SO3—X+ | SO3—X+ | POLYMER |
| 195 | SO3—X+ | SO2Me | SO3—X+ | H | POLYMER |
| 196 | SO3—X+ | SO2Me | H | SO2Me | POLYMER |
| 197 | SO3—X+ | SO2Me | H | SO3—X+ | POLYMER |
| 198 | SO3—X+ | SO2Me | H | H | POLYMER |
| 199 | SO3—X+ | SO3—X+ | SO2Me | SO2Me | POLYMER |
| 200 | SO3—X+ | SO3—X+ | SO2Me | SO3—X+ | POLYMER |
| 201 | SO3—X+ | SO3—X+ | SO2Me | H | POLYMER |
| 202 | SO3—X+ | SO3—X+ | SO3—X+ | SO2Me | POLYMER |
| 203 | SO3—X+ | SO3—X+ | SO3—X+ | SO3—X+ | POLYMER |
| 204 | SO3—X+ | SO3—X+ | SO3—X+ | H | POLYMER |
| 205 | SO3—X+ | SO3—X+ | H | SO2Me | POLYMER |
| 206 | SO3—X+ | SO3—X+ | H | SO3—X+ | POLYMER |
| 207 | SO3—X+ | SO3—X+ | H | H | POLYMER |
| 208 | SO3—X+ | H | SO2Me | SO2Me | POLYMER |
| 209 | SO3—X+ | H | SO2Me | SO3—X+ | POLYMER |
| 210 | SO3—X+ | H | SO2Me | H | POLYMER |
| 211 | SO3—X+ | H | SO3—X+ | SO2Me | POLYMER |
| 212 | SO3—X+ | H | SO3—X+ | SO3—X+ | POLYMER |
| 213 | SO3—X+ | H | SO3—X+ | H | POLYMER |
| 214 | SO3—X+ | H | H | SO2Me | POLYMER |
| 215 | SO3—X+ | H | H | SO3—X+ | POLYMER |
| 216 | SO3—X+ | H | H | H | POLYMER |
| 217 | H | SO2Me | SO2Me | SO2Me | POLYMER |
| 218 | H | SO2Me | SO2Me | SO3—X+ | POLYMER |
| 219 | H | SO2Me | SO2Me | H | POLYMER |
| 220 | H | SO2Me | SO3—X+ | SO2Me | POLYMER |
| 221 | H | SO2Me | SO3—X+ | SO3—X+ | POLYMER |
| 222 | H | SO2Me | SO3—X+ | H | POLYMER |
| 223 | H | SO2Me | H | SO2Me | POLYMER |
| 224 | H | SO2Me | H | SO3—X+ | POLYMER |
| 225 | H | SO2Me | H | H | POLYMER |
| 226 | H | SO3—X+ | SO2Me | SO2Me | POLYMER |
| 227 | H | SO3—X+ | SO2Me | SO3—X+ | POLYMER |
| 228 | H | SO3—X+ | SO2Me | H | POLYMER |
| 229 | H | SO3—X+ | SO3—X+ | SO2Me | POLYMER |
| 230 | H | SO3—X+ | SO3—X+ | SO3—X+ | POLYMER |
| 231 | H | SO3—X+ | SO3—X+ | H | POLYMER |
| 232 | H | SO3—X+ | H | SO2Me | POLYMER |
| 233 | H | SO3—X+ | H | SO3—X+ | POLYMER |
| 234 | H | SO3—X+ | H | H | POLYMER |
| 235 | H | H | SO2Me | SO2Me | POLYMER |
| 236 | H | H | SO2Me | SO3—X+ | POLYMER |
| 237 | H | H | SO2Me | H | POLYMER |
| 238 | H | H | SO3—X+ | SO2Me | POLYMER |
| 239 | H | H | SO3—X+ | SO3—X+ | POLYMER |
| 240 | H | H | SO3—X+ | H | POLYMER |

TABLE 3

Various chemical moieties for Structure 3.
COMBINATIONS FOR STRUCTURE 3

| | 2<br>A, D, H,<br>L or N | 3<br>B, E, M,<br>I or O | 4<br>F or J | 6<br>C, G,<br>K, or P | 1<br>Q |
|---|---|---|---|---|---|
| 1 | SO2Me | SO2Me | SO2Me | SO2Me | POLYMER |
| 2 | SO2Me | SO2Me | SO2Me | SO3—X+ | POLYMER |
| 3 | SO2Me | SO2Me | SO2Me | H | POLYMER |
| 4 | SO2Me | SO2Me | SO3—X+ | SO2Me | POLYMER |
| 5 | SO2Me | SO2Me | SO3—X+ | SO3—X+ | POLYMER |
| 6 | SO2Me | SO2Me | SO3—X+ | H | POLYMER |
| 7 | SO2Me | SO2Me | H | SO2Me | POLYMER |
| 8 | SO2Me | SO2Me | H | SO3—X+ | POLYMER |
| 9 | SO2Me | SO2Me | H | H | POLYMER |
| 10 | SO2Me | SO3—X+ | SO2Me | SO2Me | POLYMER |
| 11 | SO2Me | SO3—X+ | SO2Me | SO3—X+ | POLYMER |
| 12 | SO2Me | SO3—X+ | SO2Me | H | POLYMER |
| 13 | SO2Me | SO3—X+ | SO3—X+ | SO2Me | POLYMER |
| 14 | SO2Me | SO3—X+ | SO3—X+ | SO3—X+ | POLYMER |
| 15 | SO2Me | SO3—X+ | SO3—X+ | H | POLYMER |
| 16 | SO2Me | SO3—X+ | H | SO2Me | POLYMER |
| 17 | SO2Me | SO3—X+ | H | SO3—X+ | POLYMER |
| 18 | SO2Me | SO3—X+ | H | H | POLYMER |
| 19 | SO2Me | H | SO2Me | SO2Me | POLYMER |
| 20 | SO2Me | H | SO2Me | SO3—X+ | POLYMER |
| 21 | SO2Me | H | SO2Me | H | POLYMER |
| 22 | SO2Me | H | SO3—X+ | SO2Me | POLYMER |
| 23 | SO2Me | H | SO3—X+ | SO3—X+ | POLYMER |
| 24 | SO2Me | H | SO3—X+ | H | POLYMER |
| 25 | SO2Me | H | H | SO2Me | POLYMER |
| 26 | SO2Me | H | H | SO3—X+ | POLYMER |
| 27 | SO2Me | H | H | H | POLYMER |
| 28 | SO3—X+ | SO2Me | SO2Me | SO2Me | POLYMER |
| 29 | SO3—X+ | SO2Me | SO2Me | SO3—X+ | POLYMER |
| 30 | SO3—X+ | SO2Me | SO2Me | H | POLYMER |
| 31 | SO3—X+ | SO2Me | SO3—X+ | SO2Me | POLYMER |
| 32 | SO3—X+ | SO2Me | SO3—X+ | SO3—X+ | POLYMER |
| 33 | SO3—X+ | SO2Me | SO3—X+ | H | POLYMER |
| 34 | SO3—X+ | SO2Me | H | SO2Me | POLYMER |
| 35 | SO3—X+ | SO2Me | H | SO3—X+ | POLYMER |
| 36 | SO3—X+ | SO2Me | H | H | POLYMER |
| 37 | SO3—X+ | SO3—X+ | SO2Me | SO2Me | POLYMER |
| 38 | SO3—X+ | SO3—X+ | SO2Me | SO3—X+ | POLYMER |
| 39 | SO3—X+ | SO3—X+ | SO2Me | H | POLYMER |
| 40 | SO3—X+ | SO3—X+ | SO3—X+ | SO2Me | POLYMER |
| 41 | SO3—X+ | SO3—X+ | SO3—X+ | SO3—X+ | POLYMER |
| 42 | SO3—X+ | SO3—X+ | SO3—X+ | H | POLYMER |
| 43 | SO3—X+ | SO3—X+ | H | SO2Me | POLYMER |

TABLE 3-continued

Various chemical moieties for Structure 3.
COMBINATIONS FOR STRUCTURE 3

| | 2<br>A, D, H,<br>L or N | 3<br>B, E, M,<br>I or O | 4<br>F or J | 6<br>C, G,<br>K, or P | 1<br>Q |
|---|---|---|---|---|---|
| 44 | SO3—X+ | SO3—X+ | H | SO3—X+ | POLYMER |
| 45 | SO3—X+ | SO3—X+ | H | H | POLYMER |
| 46 | SO3—X+ | H | SO2Me | SO2Me | POLYMER |
| 47 | SO3—X+ | H | SO2Me | SO3—X+ | POLYMER |
| 48 | SO3—X+ | H | SO2Me | H | POLYMER |
| 49 | SO3—X+ | H | SO3—X+ | SO2Me | POLYMER |
| 50 | SO3—X+ | H | SO3—X+ | SO3—X+ | POLYMER |
| 51 | SO3—X+ | H | SO3—X+ | H | POLYMER |
| 52 | SO3—X+ | H | H | SO2Me | POLYMER |
| 53 | SO3—X+ | H | H | SO3—X+ | POLYMER |
| 54 | SO3—X+ | H | H | H | POLYMER |
| 55 | H | SO2Me | SO2Me | SO2Me | POLYMER |
| 56 | H | SO2Me | SO2Me | SO3—X+ | POLYMER |
| 57 | H | SO2Me | SO2Me | H | POLYMER |
| 58 | H | SO2Me | SO3—X+ | SO2Me | POLYMER |
| 59 | H | SO2Me | SO3—X+ | SO3—X+ | POLYMER |
| 60 | H | SO2Me | SO3—X+ | H | POLYMER |
| 61 | H | SO2Me | H | SO2Me | POLYMER |
| 62 | H | SO2Me | H | SO3—X+ | POLYMER |
| 63 | H | SO2Me | H | H | POLYMER |
| 64 | H | SO3—X+ | SO2Me | SO2Me | POLYMER |
| 65 | H | SO3—X+ | SO2Me | SO3—X+ | POLYMER |
| 66 | H | SO3—X+ | SO2Me | H | POLYMER |
| 67 | H | SO3—X+ | SO3—X+ | SO2Me | POLYMER |
| 68 | H | SO3—X+ | SO3—X+ | SO3—X+ | POLYMER |
| 69 | H | SO3—X+ | SO3—X+ | H | POLYMER |
| 70 | H | SO3—X+ | H | SO2Me | POLYMER |
| 71 | H | SO3—X+ | H | SO3—X+ | POLYMER |
| 72 | H | SO3—X+ | H | H | POLYMER |
| 73 | H | H | SO2Me | SO2Me | POLYMER |
| 74 | H | H | SO2Me | SO3—X+ | POLYMER |
| 75 | H | H | SO2Me | H | POLYMER |
| 76 | H | H | SO3—X+ | SO2Me | POLYMER |
| 77 | H | H | SO3—X+ | SO3—X+ | POLYMER |
| 78 | H | H | SO3—X+ | H | POLYMER |
| 79 | H | H | H | SO2Me | POLYMER |
| 80 | H | H | H | SO3—X+ | POLYMER |
| 81 | H | H | H | H | POLYMER |
| 82 | SO2Me | SO2Me | SO2Me | SO2Me | POLYMER |
| 83 | SO2Me | SO2Me | SO2Me | SO3—X+ | POLYMER |
| 84 | SO2Me | SO2Me | SO2Me | H | POLYMER |
| 85 | SO2Me | SO2Me | SO3—X+ | SO2Me | POLYMER |
| 86 | SO2Me | SO2Me | SO3—X+ | SO3—X+ | POLYMER |
| 87 | SO2Me | SO2Me | SO3—X+ | H | POLYMER |
| 88 | SO2Me | SO2Me | H | SO2Me | POLYMER |
| 89 | SO2Me | SO2Me | H | SO3—X+ | POLYMER |
| 90 | SO2Me | SO2Me | H | H | POLYMER |
| 91 | SO2Me | SO3—X+ | SO2Me | SO2Me | POLYMER |
| 92 | SO2Me | SO3—X+ | SO2Me | SO3—X+ | POLYMER |
| 93 | SO2Me | SO3—X+ | SO2Me | H | POLYMER |
| 94 | SO2Me | SO3—X+ | SO3—X+ | SO2Me | POLYMER |
| 95 | SO2Me | SO3—X+ | SO3—X+ | SO3—X+ | POLYMER |
| 96 | SO2Me | SO3—X+ | SO3—X+ | H | POLYMER |
| 97 | SO2Me | SO3—X+ | H | SO2Me | POLYMER |
| 98 | SO2Me | SO3—X+ | H | SO3—X+ | POLYMER |
| 99 | SO2Me | SO3—X+ | H | H | POLYMER |
| 100 | SO2Me | H | SO2Me | SO2Me | POLYMER |
| 101 | SO2Me | H | SO2Me | SO3—X+ | POLYMER |
| 102 | SO2Me | H | SO2Me | H | POLYMER |
| 103 | SO2Me | H | SO3—X+ | SO2Me | POLYMER |
| 104 | SO2Me | H | SO3—X+ | SO3—X+ | POLYMER |
| 105 | SO2Me | H | SO3—X+ | H | POLYMER |
| 106 | SO2Me | H | H | SO2Me | POLYMER |
| 107 | SO2Me | H | H | SO3—X+ | POLYMER |
| 108 | SO2Me | H | H | H | POLYMER |
| 109 | SO3—X+ | SO2Me | SO2Me | SO2Me | POLYMER |
| 110 | SO3—X+ | SO2Me | SO2Me | SO3—X+ | POLYMER |
| 111 | SO3—X+ | SO2Me | SO2Me | H | POLYMER |
| 112 | SO3—X+ | SO2Me | SO3—X+ | SO2Me | POLYMER |
| 113 | SO3—X+ | SO2Me | SO3—X+ | SO3—X+ | POLYMER |
| 114 | SO3—X+ | SO2Me | SO3—X+ | H | POLYMER |
| 115 | SO3—X+ | SO2Me | H | SO2Me | POLYMER |
| 116 | SO3—X+ | SO2Me | H | SO3—X+ | POLYMER |
| 117 | SO3—X+ | SO2Me | H | H | POLYMER |
| 118 | SO3—X+ | SO3—X+ | SO2Me | SO2Me | POLYMER |
| 119 | SO3—X+ | SO3—X+ | SO2Me | SO3—X+ | POLYMER |
| 120 | SO3—X+ | SO3—X+ | SO2Me | H | POLYMER |
| 121 | SO3—X+ | SO3—X+ | SO3—X+ | SO2Me | POLYMER |
| 122 | SO3—X+ | SO3—X+ | SO3—X+ | SO3—X+ | POLYMER |
| 123 | SO3—X+ | SO3—X+ | SO3—X+ | H | POLYMER |
| 124 | SO3—X+ | SO3—X+ | H | SO2Me | POLYMER |
| 125 | SO3—X+ | SO3—X+ | H | SO3—X+ | POLYMER |
| 126 | SO3—X+ | SO3—X+ | H | H | POLYMER |
| 127 | SO3—X+ | H | SO2Me | SO2Me | POLYMER |
| 128 | SO3—X+ | H | SO2Me | SO3—X+ | POLYMER |
| 129 | SO3—X+ | H | SO2Me | H | POLYMER |
| 130 | SO3—X+ | H | SO3—X+ | SO2Me | POLYMER |
| 131 | SO3—X+ | H | SO3—X+ | SO3—X+ | POLYMER |
| 132 | SO3—X+ | H | SO3—X+ | H | POLYMER |
| 133 | SO3—X+ | H | H | SO2Me | POLYMER |
| 134 | SO3—X+ | H | H | SO3—X+ | POLYMER |
| 135 | SO3—X+ | H | H | H | POLYMER |
| 136 | H | SO2Me | SO2Me | SO2Me | POLYMER |
| 137 | H | SO2Me | SO2Me | SO3—X+ | POLYMER |
| 138 | H | SO2Me | SO2Me | H | POLYMER |
| 139 | H | SO2Me | SO3—X+ | SO2Me | POLYMER |
| 140 | H | SO2Me | SO3—X+ | SO3—X+ | POLYMER |
| 141 | H | SO2Me | SO3—X+ | H | POLYMER |
| 142 | H | SO2Me | H | SO2Me | POLYMER |
| 143 | H | SO2Me | H | SO3—X+ | POLYMER |
| 144 | H | SO2Me | H | H | POLYMER |
| 145 | H | SO3—X+ | SO2Me | SO2Me | POLYMER |
| 146 | H | SO3—X+ | SO2Me | SO3—X+ | POLYMER |
| 147 | H | SO3—X+ | SO2Me | H | POLYMER |
| 148 | H | SO3—X+ | SO3—X+ | SO2Me | POLYMER |
| 149 | H | SO3—X+ | SO3—X+ | SO3—X+ | POLYMER |
| 150 | H | SO3—X+ | SO3—X+ | H | POLYMER |
| 151 | H | SO3—X+ | H | SO2Me | POLYMER |
| 152 | H | SO3—X+ | H | SO3—X+ | POLYMER |
| 153 | H | SO3—X+ | H | H | POLYMER |
| 154 | H | H | SO2Me | SO2Me | POLYMER |
| 155 | H | H | SO2Me | SO3—X+ | POLYMER |
| 156 | H | H | SO2Me | H | POLYMER |
| 157 | H | H | SO3—X+ | SO2Me | POLYMER |
| 158 | H | H | SO3—X+ | SO3—X+ | POLYMER |
| 159 | H | H | SO3—X+ | H | POLYMER |
| 160 | H | H | H | SO2Me | POLYMER |
| 161 | H | H | H | SO3—X+ | POLYMER |
| 162 | H | H | H | H | POLYMER |
| 163 | SO2Me | SO2Me | SO2Me | SO2Me | POLYMER |
| 164 | SO2Me | SO2Me | SO2Me | SO3—X+ | POLYMER |
| 165 | SO2Me | SO2Me | SO2Me | H | POLYMER |
| 166 | SO2Me | SO2Me | SO3—X+ | SO2Me | POLYMER |
| 167 | SO2Me | SO2Me | SO3—X+ | SO3—X+ | POLYMER |
| 168 | SO2Me | SO2Me | SO3—X+ | H | POLYMER |
| 169 | SO2Me | SO2Me | H | SO2Me | POLYMER |
| 170 | SO2Me | SO2Me | H | SO3—X+ | POLYMER |
| 171 | SO2Me | SO2Me | H | H | POLYMER |
| 172 | SO2Me | SO3—X+ | SO2Me | SO2Me | POLYMER |
| 173 | SO2Me | SO3—X+ | SO2Me | SO3—X+ | POLYMER |
| 174 | SO2Me | SO3—X+ | SO2Me | H | POLYMER |
| 175 | SO2Me | SO3—X+ | SO3—X+ | SO2Me | POLYMER |
| 176 | SO2Me | SO3—X+ | SO3—X+ | SO3—X+ | POLYMER |
| 177 | SO2Me | SO3—X+ | SO3—X+ | H | POLYMER |
| 178 | SO2Me | SO3—X+ | H | SO2Me | POLYMER |
| 179 | SO2Me | SO3—X+ | H | SO3—X+ | POLYMER |
| 180 | SO2Me | SO3—X+ | H | H | POLYMER |
| 181 | SO2Me | H | SO2Me | SO2Me | POLYMER |
| 182 | SO2Me | H | SO2Me | SO3—X+ | POLYMER |
| 183 | SO2Me | H | SO2Me | H | POLYMER |
| 184 | SO2Me | H | SO3—X+ | SO2Me | POLYMER |
| 185 | SO2Me | H | SO3—X+ | SO3—X+ | POLYMER |
| 186 | SO2Me | H | SO3—X+ | H | POLYMER |
| 187 | SO2Me | H | H | SO2Me | POLYMER |
| 188 | SO2Me | H | H | SO3—X+ | POLYMER |
| 189 | SO2Me | H | H | H | POLYMER |

TABLE 3-continued

Various chemical moieties for Structure 3.
COMBINATIONS FOR STRUCTURE 3

| | 2<br>A, D, H,<br>L or N | 3<br>B, E, M,<br>I or O | 4<br>F or J | 6<br>C, G,<br>K, or P | 1<br>Q |
|---|---|---|---|---|---|
| 190 | SO3—X+ | SO2Me | SO2Me | SO2Me | POLYMER |
| 191 | SO3—X+ | SO2Me | SO2Me | SO3—X+ | POLYMER |
| 192 | SO3—X+ | SO2Me | SO2Me | H | POLYMER |
| 193 | SO3—X+ | SO2Me | SO3—X+ | SO2Me | POLYMER |
| 194 | SO3—X+ | SO2Me | SO3—X+ | SO3—X+ | POLYMER |
| 195 | SO3—X+ | SO2Me | SO3—X+ | H | POLYMER |
| 196 | SO3—X+ | SO2Me | H | SO2Me | POLYMER |
| 197 | SO3—X+ | SO2Me | H | SO3—X+ | POLYMER |
| 198 | SO3—X+ | SO2Me | H | H | POLYMER |
| 199 | SO3—X+ | SO3—X+ | SO2Me | SO2Me | POLYMER |
| 200 | SO3—X+ | SO3—X+ | SO2Me | SO3—X+ | POLYMER |
| 201 | SO3—X+ | SO3—X+ | SO2Me | H | POLYMER |
| 202 | SO3—X+ | SO3—X+ | SO3—X+ | SO2Me | POLYMER |
| 203 | SO3—X+ | SO3—X+ | SO3—X+ | SO3—X+ | POLYMER |
| 204 | SO3—X+ | SO3—X+ | SO3—X+ | H | POLYMER |
| 205 | SO3—X+ | SO3—X+ | H | SO2Me | POLYMER |
| 206 | SO3—X+ | SO3—X+ | H | SO3—X+ | POLYMER |
| 207 | SO3—X+ | SO3—X+ | H | H | POLYMER |
| 208 | SO3—X+ | H | SO2Me | SO2Me | POLYMER |
| 209 | SO3—X+ | H | SO2Me | SO3—X+ | POLYMER |
| 210 | SO3—X+ | H | SO2Me | H | POLYMER |
| 211 | SO3—X+ | H | SO3—X+ | SO2Me | POLYMER |
| 212 | SO3—X+ | H | SO3—X+ | SO3—X+ | POLYMER |
| 213 | SO3—X+ | H | SO3—X+ | H | POLYMER |
| 214 | SO3—X+ | H | H | SO2Me | POLYMER |
| 215 | SO3—X+ | H | H | SO3—X+ | POLYMER |
| 216 | SO3—X+ | H | H | H | POLYMER |
| 217 | H | SO2Me | SO2Me | SO2Me | POLYMER |
| 218 | H | SO2Me | SO2Me | SO3—X+ | POLYMER |
| 219 | H | SO2Me | SO2Me | H | POLYMER |
| 220 | H | SO2Me | SO3—X+ | SO2Me | POLYMER |
| 221 | H | SO2Me | SO3—X+ | SO3—X+ | POLYMER |
| 222 | H | SO2Me | SO3—X+ | H | POLYMER |
| 223 | H | SO2Me | H | SO2Me | POLYMER |
| 224 | H | SO2Me | H | SO3—X+ | POLYMER |
| 225 | H | SO2Me | H | H | POLYMER |
| 226 | H | SO3—X+ | SO2Me | SO2Me | POLYMER |
| 227 | H | SO3—X+ | SO2Me | SO3—X+ | POLYMER |
| 228 | H | SO3—X+ | SO2Me | H | POLYMER |
| 229 | H | SO3—X+ | SO3—X+ | SO2Me | POLYMER |
| 230 | H | SO3—X+ | SO3—X+ | SO3—X+ | POLYMER |
| 231 | H | SO3—X+ | SO3—X+ | H | POLYMER |
| 232 | H | SO3—X+ | H | SO2Me | POLYMER |
| 233 | H | SO3—X+ | H | SO3—X+ | POLYMER |
| 234 | H | SO3—X+ | H | H | POLYMER |
| 235 | H | H | SO2Me | SO2Me | POLYMER |
| 236 | H | H | SO2Me | SO3—X+ | POLYMER |
| 237 | H | H | SO2Me | H | POLYMER |
| 238 | H | H | SO3—X+ | SO2Me | POLYMER |
| 239 | H | H | SO3—X+ | SO3—X+ | POLYMER |
| 240 | H | H | SO3—X+ | H | POLYMER |

TABLE 4

Various chemical moieties for Structure 4.
COMBINATIONS FOR STRUCTURE 4

| | 2<br>A, E, I, or K | 3<br>B, F, J or L | 4<br>G or C | 6<br>D, H or M | 1<br>Q |
|---|---|---|---|---|---|
| 1 | SO2Me | SO2Me | SO2Me | SO2Me | POLYMER |
| 2 | SO2Me | SO2Me | SO2Me | SO3—X+ | POLYMER |
| 3 | SO2Me | SO2Me | SO2Me | H | POLYMER |
| 4 | SO2Me | SO2Me | SO3—X+ | SO2Me | POLYMER |
| 5 | SO2Me | SO2Me | SO3—X+ | SO3—X+ | POLYMER |
| 6 | SO2Me | SO2Me | SO3—X+ | H | POLYMER |
| 7 | SO2Me | SO2Me | H | SO2Me | POLYMER |
| 8 | SO2Me | SO2Me | H | SO3—X+ | POLYMER |
| 9 | SO2Me | SO2Me | H | H | POLYMER |
| 10 | SO2Me | SO3—X+ | SO2Me | SO2Me | POLYMER |
| 11 | SO2Me | SO3—X+ | SO2Me | SO3—X+ | POLYMER |
| 12 | SO2Me | SO3—X+ | SO2Me | H | POLYMER |
| 13 | SO2Me | SO3—X+ | SO3—X+ | SO2Me | POLYMER |
| 14 | SO2Me | SO3—X+ | SO3—X+ | SO3—X+ | POLYMER |
| 15 | SO2Me | SO3—X+ | SO3—X+ | H | POLYMER |
| 16 | SO2Me | SO3—X+ | H | SO2Me | POLYMER |
| 17 | SO2Me | SO3—X+ | H | SO3—X+ | POLYMER |
| 18 | SO2Me | SO3—X+ | H | H | POLYMER |
| 19 | SO2Me | H | SO2Me | SO2Me | POLYMER |
| 20 | SO2Me | H | SO2Me | SO3—X+ | POLYMER |
| 21 | SO2Me | H | SO2Me | H | POLYMER |
| 22 | SO2Me | H | SO3—X+ | SO2Me | POLYMER |
| 23 | SO2Me | H | SO3—X+ | SO3—X+ | POLYMER |
| 24 | SO2Me | H | SO3—X+ | H | POLYMER |
| 25 | SO2Me | H | H | SO2Me | POLYMER |
| 26 | SO2Me | H | H | SO3—X+ | POLYMER |
| 27 | SO2Me | H | H | H | POLYMER |
| 28 | SO3—X+ | SO2Me | SO2Me | SO2Me | POLYMER |
| 29 | SO3—X+ | SO2Me | SO2Me | SO3—X+ | POLYMER |
| 30 | SO3—X+ | SO2Me | SO2Me | H | POLYMER |
| 31 | SO3—X+ | SO2Me | SO3—X+ | SO2Me | POLYMER |
| 32 | SO3—X+ | SO2Me | SO3—X+ | SO3—X+ | POLYMER |
| 33 | SO3—X+ | SO2Me | SO3—X+ | H | POLYMER |
| 34 | SO3—X+ | SO2Me | H | SO2Me | POLYMER |
| 35 | SO3—X+ | SO2Me | H | SO3—X+ | POLYMER |
| 36 | SO3—X+ | SO2Me | H | H | POLYMER |
| 37 | SO3—X+ | SO3—X+ | SO2Me | SO2Me | POLYMER |
| 38 | SO3—X+ | SO3—X+ | SO2Me | SO3—X+ | POLYMER |
| 39 | SO3—X+ | SO3—X+ | SO2Me | H | POLYMER |
| 40 | SO3—X+ | SO3—X+ | SO3—X+ | SO2Me | POLYMER |
| 41 | SO3—X+ | SO3—X+ | SO3—X+ | SO3—X+ | POLYMER |
| 42 | SO3—X+ | SO3—X+ | SO3—X+ | H | POLYMER |
| 43 | SO3—X+ | SO3—X+ | H | SO2Me | POLYMER |
| 44 | SO3—X+ | SO3—X+ | H | SO3—X+ | POLYMER |
| 45 | SO3—X+ | SO3—X+ | H | H | POLYMER |
| 46 | SO3—X+ | H | SO2Me | SO2Me | POLYMER |
| 47 | SO3—X+ | H | SO2Me | SO3—X+ | POLYMER |
| 48 | SO3—X+ | H | SO2Me | H | POLYMER |
| 49 | SO3—X+ | H | SO3—X+ | SO2Me | POLYMER |
| 50 | SO3—X+ | H | SO3—X+ | SO3—X+ | POLYMER |
| 51 | SO3—X+ | H | SO3—X+ | H | POLYMER |
| 52 | SO3—X+ | H | H | SO2Me | POLYMER |
| 53 | SO3—X+ | H | H | SO3—X+ | POLYMER |
| 54 | SO3—X+ | H | H | H | POLYMER |
| 55 | H | SO2Me | SO2Me | SO2Me | POLYMER |
| 56 | H | SO2Me | SO2Me | SO3—X+ | POLYMER |
| 57 | H | SO2Me | SO2Me | H | POLYMER |
| 58 | H | SO2Me | SO3—X+ | SO2Me | POLYMER |
| 59 | H | SO2Me | SO3—X+ | SO3—X+ | POLYMER |
| 60 | H | SO2Me | SO3—X+ | H | POLYMER |
| 61 | H | SO2Me | H | SO2Me | POLYMER |
| 62 | H | SO2Me | H | SO3—X+ | POLYMER |
| 63 | H | SO2Me | H | H | POLYMER |
| 64 | H | SO3—X+ | SO2Me | SO2Me | POLYMER |
| 65 | H | SO3—X+ | SO2Me | SO3—X+ | POLYMER |
| 66 | H | SO3—X+ | SO2Me | H | POLYMER |
| 67 | H | SO3—X+ | SO3—X+ | SO2Me | POLYMER |
| 68 | H | SO3—X+ | SO3—X+ | SO3—X+ | POLYMER |
| 69 | H | SO3—X+ | SO3—X+ | H | POLYMER |
| 70 | H | SO3—X+ | H | SO2Me | POLYMER |
| 71 | H | SO3—X+ | H | SO3—X+ | POLYMER |
| 72 | H | SO3—X+ | H | H | POLYMER |
| 73 | H | H | SO2Me | SO2Me | POLYMER |
| 74 | H | H | SO2Me | SO3—X+ | POLYMER |
| 75 | H | H | SO2Me | H | POLYMER |
| 76 | H | H | SO3—X+ | SO2Me | POLYMER |
| 77 | H | H | SO3—X+ | SO3—X+ | POLYMER |
| 78 | H | H | SO3—X+ | H | POLYMER |
| 79 | H | H | H | SO2Me | POLYMER |
| 80 | H | H | H | SO3—X+ | POLYMER |
| 81 | H | H | H | H | POLYMER |
| 82 | SO2Me | SO2Me | SO2Me | SO2Me | POLYMER |
| 83 | SO2Me | SO2Me | SO2Me | SO3—X+ | POLYMER |
| 84 | SO2Me | SO2Me | SO2Me | H | POLYMER |

TABLE 4-continued

Various chemical moieties for Structure 4.
COMBINATIONS FOR STRUCTURE 4

| | 2<br>A, E, I, or K | 3<br>B, F, J or L | 4<br>G or C | 6<br>D, H or M | 1<br>Q |
|---|---|---|---|---|---|
| 85 | SO2Me | SO2Me | SO3—X+ | SO2Me | POLYMER |
| 86 | SO2Me | SO2Me | SO3—X+ | SO3—X+ | POLYMER |
| 87 | SO2Me | SO2Me | SO3—X+ | H | POLYMER |
| 88 | SO2Me | SO2Me | H | SO2Me | POLYMER |
| 89 | SO2Me | SO2Me | H | SO3—X+ | POLYMER |
| 90 | SO2Me | SO2Me | H | H | POLYMER |
| 91 | SO2Me | SO3—X+ | SO2Me | SO2Me | POLYMER |
| 92 | SO2Me | SO3—X+ | SO2Me | SO3—X+ | POLYMER |
| 93 | SO2Me | SO3—X+ | SO2Me | H | POLYMER |
| 94 | SO2Me | SO3—X+ | SO3—X+ | SO2Me | POLYMER |
| 95 | SO2Me | SO3—X+ | SO3—X+ | SO3—X+ | POLYMER |
| 96 | SO2Me | SO3—X+ | SO3—X+ | H | POLYMER |
| 97 | SO2Me | SO3—X+ | H | SO2Me | POLYMER |
| 98 | SO2Me | SO3—X+ | H | SO3—X+ | POLYMER |
| 99 | SO2Me | SO3—X+ | H | H | POLYMER |
| 100 | SO2Me | H | SO2Me | SO2Me | POLYMER |
| 101 | SO2Me | H | SO2Me | SO3—X+ | POLYMER |
| 102 | SO2Me | H | SO2Me | H | POLYMER |
| 103 | SO2Me | H | SO3—X+ | SO2Me | POLYMER |
| 104 | SO2Me | H | SO3—X+ | SO3—X+ | POLYMER |
| 105 | SO2Me | H | SO3—X+ | H | POLYMER |
| 106 | SO2Me | H | H | SO2Me | POLYMER |
| 107 | SO2Me | H | H | SO3—X+ | POLYMER |
| 108 | SO2Me | H | H | H | POLYMER |
| 109 | SO3—X+ | SO2Me | SO2Me | SO2Me | POLYMER |
| 110 | SO3—X+ | SO2Me | SO2Me | SO3—X+ | POLYMER |
| 111 | SO3—X+ | SO2Me | SO2Me | H | POLYMER |
| 112 | SO3—X+ | SO2Me | SO3—X+ | SO2Me | POLYMER |
| 113 | SO3—X+ | SO2Me | SO3—X+ | SO3—X+ | POLYMER |
| 114 | SO3—X+ | SO2Me | SO3—X+ | H | POLYMER |
| 115 | SO3—X+ | SO2Me | H | SO2Me | POLYMER |
| 116 | SO3—X+ | SO2Me | H | SO3—X+ | POLYMER |
| 117 | SO3—X+ | SO2Me | H | H | POLYMER |
| 118 | SO3—X+ | SO3—X+ | SO2Me | SO2Me | POLYMER |
| 119 | SO3—X+ | SO3—X+ | SO2Me | SO3—X+ | POLYMER |
| 120 | SO3—X+ | SO3—X+ | SO2Me | H | POLYMER |
| 121 | SO3—X+ | SO3—X+ | SO3—X+ | SO2Me | POLYMER |
| 122 | SO3—X+ | SO3—X+ | SO3—X+ | SO3—X+ | POLYMER |
| 123 | SO3—X+ | SO3—X+ | SO3—X+ | H | POLYMER |
| 124 | SO3—X+ | SO3—X+ | H | SO2Me | POLYMER |
| 125 | SO3—X+ | SO3—X+ | H | SO3—X+ | POLYMER |
| 126 | SO3—X+ | SO3—X+ | H | H | POLYMER |
| 127 | SO3—X+ | H | SO2Me | SO2Me | POLYMER |
| 128 | SO3—X+ | H | SO2Me | SO3—X+ | POLYMER |
| 129 | SO3—X+ | H | SO2Me | H | POLYMER |
| 130 | SO3—X+ | H | SO3—X+ | SO2Me | POLYMER |
| 131 | SO3—X+ | H | SO3—X+ | SO3—X+ | POLYMER |
| 132 | SO3—X+ | H | SO3—X+ | H | POLYMER |
| 133 | SO3—X+ | H | H | SO2Me | POLYMER |
| 134 | SO3—X+ | H | H | SO3—X+ | POLYMER |
| 135 | SO3—X+ | H | H | H | POLYMER |
| 136 | H | SO2Me | SO2Me | SO2Me | POLYMER |
| 137 | H | SO2Me | SO2Me | SO3—X+ | POLYMER |
| 138 | H | SO2Me | SO2Me | H | POLYMER |
| 139 | H | SO2Me | SO3—X+ | SO2Me | POLYMER |
| 140 | H | SO2Me | SO3—X+ | SO3—X+ | POLYMER |
| 141 | H | SO2Me | SO3—X+ | H | POLYMER |
| 142 | H | SO2Me | H | SO2Me | POLYMER |
| 143 | H | SO2Me | H | SO3—X+ | POLYMER |
| 144 | H | SO2Me | H | H | POLYMER |
| 145 | H | SO3—X+ | SO2Me | SO2Me | POLYMER |
| 146 | H | SO3—X+ | SO2Me | SO3—X+ | POLYMER |
| 147 | H | SO3—X+ | SO2Me | H | POLYMER |
| 148 | H | SO3—X+ | SO3—X+ | SO2Me | POLYMER |
| 149 | H | SO3—X+ | SO3—X+ | SO3—X+ | POLYMER |
| 150 | H | SO3—X+ | SO3—X+ | H | POLYMER |
| 151 | H | SO3—X+ | H | SO2Me | POLYMER |
| 152 | H | SO3—X+ | H | SO3—X+ | POLYMER |
| 153 | H | SO3—X+ | H | H | POLYMER |
| 154 | H | H | SO2Me | SO2Me | POLYMER |
| 155 | H | H | SO2Me | SO3—X+ | POLYMER |
| 156 | H | H | SO2Me | H | POLYMER |
| 157 | H | H | SO3—X+ | SO2Me | POLYMER |
| 158 | H | H | SO3—X+ | SO3—X+ | POLYMER |
| 159 | H | H | SO3—X+ | H | POLYMER |
| 160 | H | H | H | SO2Me | POLYMER |
| 161 | H | H | H | SO3—X+ | POLYMER |
| 162 | H | H | H | H | POLYMER |
| 163 | SO2Me | SO2Me | SO2Me | SO2Me | POLYMER |
| 164 | SO2Me | SO2Me | SO2Me | SO3—X+ | POLYMER |
| 165 | SO2Me | SO2Me | SO2Me | H | POLYMER |
| 166 | SO2Me | SO2Me | SO3—X+ | SO2Me | POLYMER |
| 167 | SO2Me | SO2Me | SO3—X+ | SO3—X+ | POLYMER |
| 168 | SO2Me | SO2Me | SO3—X+ | H | POLYMER |
| 169 | SO2Me | SO2Me | H | SO2Me | POLYMER |
| 170 | SO2Me | SO2Me | H | SO3—X+ | POLYMER |
| 171 | SO2Me | SO2Me | H | H | POLYMER |
| 172 | SO2Me | SO3—X+ | SO2Me | SO2Me | POLYMER |
| 173 | SO2Me | SO3—X+ | SO2Me | SO3—X+ | POLYMER |
| 174 | SO2Me | SO3—X+ | SO2Me | H | POLYMER |
| 175 | SO2Me | SO3—X+ | SO3—X+ | SO2Me | POLYMER |
| 176 | SO2Me | SO3—X+ | SO3—X+ | SO3—X+ | POLYMER |
| 177 | SO2Me | SO3—X+ | SO3—X+ | H | POLYMER |
| 178 | SO2Me | SO3—X+ | H | SO2Me | POLYMER |
| 179 | SO2Me | SO3—X+ | H | SO3—X+ | POLYMER |
| 180 | SO2Me | SO3—X+ | H | H | POLYMER |
| 181 | SO2Me | H | SO2Me | SO2Me | POLYMER |
| 182 | SO2Me | H | SO2Me | SO3—X+ | POLYMER |
| 183 | SO2Me | H | SO2Me | H | POLYMER |
| 184 | SO2Me | H | SO3—X+ | SO2Me | POLYMER |
| 185 | SO2Me | H | SO3—X+ | SO3—X+ | POLYMER |
| 186 | SO2Me | H | SO3—X+ | H | POLYMER |
| 187 | SO2Me | H | H | SO2Me | POLYMER |
| 188 | SO2Me | H | H | SO3—X+ | POLYMER |
| 189 | SO2Me | H | H | H | POLYMER |
| 190 | SO3—X+ | SO2Me | SO2Me | SO2Me | POLYMER |
| 191 | SO3—X+ | SO2Me | SO2Me | SO3—X+ | POLYMER |
| 192 | SO3—X+ | SO2Me | SO2Me | H | POLYMER |
| 193 | SO3—X+ | SO2Me | SO3—X+ | SO2Me | POLYMER |
| 194 | SO3—X+ | SO2Me | SO3—X+ | SO3—X+ | POLYMER |
| 195 | SO3—X+ | SO2Me | SO3—X+ | H | POLYMER |
| 196 | SO3—X+ | SO2Me | H | SO2Me | POLYMER |
| 197 | SO3—X+ | SO2Me | H | SO3—X+ | POLYMER |
| 198 | SO3—X+ | SO2Me | H | H | POLYMER |
| 199 | SO3—X+ | SO3—X+ | SO2Me | SO2Me | POLYMER |
| 200 | SO3—X+ | SO3—X+ | SO2Me | SO3—X+ | POLYMER |
| 201 | SO3—X+ | SO3—X+ | SO2Me | H | POLYMER |
| 202 | SO3—X+ | SO3—X+ | SO3—X+ | SO2Me | POLYMER |
| 203 | SO3—X+ | SO3—X+ | SO3—X+ | SO3—X+ | POLYMER |
| 204 | SO3—X+ | SO3—X+ | SO3—X+ | H | POLYMER |
| 205 | SO3—X+ | SO3—X+ | H | SO2Me | POLYMER |
| 206 | SO3—X+ | SO3—X+ | H | SO3—X+ | POLYMER |
| 207 | SO3—X+ | SO3—X+ | H | H | POLYMER |
| 208 | SO3—X+ | H | SO2Me | SO2Me | POLYMER |
| 209 | SO3—X+ | H | SO2Me | SO3—X+ | POLYMER |
| 210 | SO3—X+ | H | SO2Me | H | POLYMER |
| 211 | SO3—X+ | H | SO3—X+ | SO2Me | POLYMER |
| 212 | SO3—X+ | H | SO3—X+ | SO3—X+ | POLYMER |
| 213 | SO3—X+ | H | SO3—X+ | H | POLYMER |
| 214 | SO3—X+ | H | H | SO2Me | POLYMER |
| 215 | SO3—X+ | H | H | SO3—X+ | POLYMER |
| 216 | SO3—X+ | H | H | H | POLYMER |
| 217 | H | SO2Me | SO2Me | SO2Me | POLYMER |
| 218 | H | SO2Me | SO2Me | SO3—X+ | POLYMER |
| 219 | H | SO2Me | SO2Me | H | POLYMER |
| 220 | H | SO2Me | SO3—X+ | SO2Me | POLYMER |
| 221 | H | SO2Me | SO3—X+ | SO3—X+ | POLYMER |
| 222 | H | SO2Me | SO3—X+ | H | POLYMER |
| 223 | H | SO2Me | H | SO2Me | POLYMER |
| 224 | H | SO2Me | H | SO3—X+ | POLYMER |
| 225 | H | SO2Me | H | H | POLYMER |
| 226 | H | SO3—X+ | SO2Me | SO2Me | POLYMER |
| 227 | H | SO3—X+ | SO2Me | SO3—X+ | POLYMER |
| 228 | H | SO3—X+ | SO2Me | H | POLYMER |
| 229 | H | SO3—X+ | SO3—X+ | SO2Me | POLYMER |
| 230 | H | SO3—X+ | SO3—X+ | SO3—X+ | POLYMER |
| 231 | H | SO3—X+ | SO3—X+ | H | POLYMER |
| 232 | H | SO3—X+ | H | SO2Me | POLYMER |

TABLE 4-continued

Various chemical moieties for Structure 4.
COMBINATIONS FOR STRUCTURE 4

| | 2<br>A, E, I, or K | 3<br>B, F, J or L | 4<br>G or C | 6<br>D, H or M | 1<br>Q |
|---|---|---|---|---|---|
| 233 | H | SO3—X+ | H | SO3—X+ | POLYMER |
| 234 | H | SO3—X+ | H | H | POLYMER |
| 235 | H | H | SO2Me | SO2Me | POLYMER |
| 236 | H | H | SO2Me | SO3—X+ | POLYMER |
| 237 | H | H | SO2Me | H | POLYMER |
| 238 | H | H | SO3—X+ | SO2Me | POLYMER |
| 239 | H | H | SO3—X+ | SO3—X+ | POLYMER |
| 240 | H | H | SO3—X+ | H | POLYMER |

TABLE 5

P24 values (pg/ml) as a measurement of HIV concentration.
RESULTING P24 VALUES (pg/ml) AS MEASUREMENT OF HIV
CONCENTRATION FOR THE INDICATED CONCENTRATIONS
OF THREE SEPARATE EFFICACY TESTS

| | CONC ($\mu$M) | | | | | | |
|---|---|---|---|---|---|---|---|
| | 0.0 | 0.32 | 1.0 | 3.2 | 10 | 32 | 100 |
| SAMPLE 1 | 594.8 | 665.0 | 356.1 | 2.6 | −21 | −29 | −42 |
| SAMPLE 2 | 809.6 | 672.3 | 407.1 | 0.8 | −7.1 | 0.2 | −26 |
| SAMPLE 3 | 669.2 | 654.6 | 351.2 | 13.0 | 10.0 | 3.3 | −13 |
| MEAN | 691.2 | 664.0 | 371.5 | 5.5 | −6.1 | −8.8 | −27 |
| % VIRAL CONCENTRATION | 100.0 | 96.1 | 53.7 | 0.8 | −0.9 | −1.3 | −3.9 |

RESULTING AVERAGE INHIBITORY CONCENTRATION 50% ($\mu$M) = 1.16

The invention claimed is:

1. A branched polysaccharide derivative containing at least one sulfate group, at least one alkylsulfate group, and at least one sulfurtrioxide pyridine group.

2. The compound of claim 1, wherein the polysaccharide is selected from the group consisting of dextrin, dextran, and cyclodextrin.

3. The compound of claim 1, wherein the at least one alkylsulfate group is selected from the group consisting of methylsulfate, ethylsulfate and propylsulfate.

4. A pharmaceutical composition unit dosage form comprising an active agent, present in an amount sufficient to provide antiviral activity, said active agent selected from the group consisting of alkylsulfate derivative of sulfated dextrin and alkylsulfate derivative of sulfated dextran wherein said active agent is branched and further contains at least one sulfurtrioxide pyridine group, and at least one excipient.

5. The pharmaceutical composition unit dosage form of claim 4, wherein the active agent is a methyl sulfate derivative.

6. The pharmaceutical composition unit dosage form of claim 4, wherein the active agent is an ethyl sulfate derivative.

7. The pharmaceutical composition unit dosage form of claim 4, wherein the active agent is a propyl sulfate derivative.

8. A method of treating HIV infection comprising administering to a patient in need thereof a therapeutically effective amount of an active agent selected from the group consisting of alkylsulfate derivative of sulfated dextrin and alkylsulfate derivative of sulfated dextran wherein said active agent also is branched and contains a sulfurtrioxide pyridine group.

9. The method of claim 8, wherein the active agent is a methyl sulfate derivative.

10. The method of claim 8, wherein the active agent is an ethyl sulfate derivative.

11. The method of claim 8, wherein the active agent is a propyl sulfate derivative.

12. The method of claim 8, wherein the administering is selected from the group consisting of oral administering, topical administering, subcutaneous administering, administering by muscular injection, administering by intraperitoneal injection and administering by intravenous injection.

* * * * *